United States Patent
Cheng et al.

(10) Patent No.: US 10,080,530 B2
(45) Date of Patent: Sep. 25, 2018

(54) PERIODIC INACTIVITY ALERTS AND ACHIEVEMENT MESSAGES

(71) Applicant: Fitbit, Inc., San Francisco, CA (US)

(72) Inventors: Yeqing Cheng, San Francisco, CA (US); Yasaman Baiani, San Francisco, CA (US); Jacob Antony Arnold, San Francisco, CA (US); Allison Maya Russell, San Francisco, CA (US); Alan McLean, San Francisco, CA (US); Delisa Lopez, San Francisco, CA (US); Nicholas Myers, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/048,980

(22) Filed: Feb. 19, 2016

(65) Prior Publication Data
US 2017/0238881 A1    Aug. 24, 2017

(51) Int. Cl.
*A61B 5/103*    (2006.01)
*A61B 5/117*    (2016.01)
(Continued)

(52) U.S. Cl.
CPC ............ *A61B 5/746* (2013.01); *A61B 5/0004* (2013.01); *A61B 5/02438* (2013.01);
(Continued)

(58) Field of Classification Search
CPC ...................................... A61B 5/00
(Continued)

(56) References Cited

U.S. PATENT DOCUMENTS

| 2,717,736 A | 9/1955 | Schlesinger |
| 2,827,309 A | 3/1958 | Fred |

(Continued)

FOREIGN PATENT DOCUMENTS

| CN | 102111434 | 6/2011 |
| CN | 102377815 | 3/2012 |

(Continued)

OTHER PUBLICATIONS

Chandrasekar et al., "Plug-and-Play, Single-Chip Photoplethysmography", 34th Annual International Conference of the IEEE EMBS, San Diego, California USA, Aug. 28-Sep. 1, 2012, 4 pages.

(Continued)

*Primary Examiner* — May Abouelela
(74) *Attorney, Agent, or Firm* — Knobbe, Martens, Olson & Bear, LLP

(57) ABSTRACT

Methods, systems, and computer programs are presented for generating alarms and congratulatory messages to reduce sedentary time. One method includes an operation for capturing motion data using an activity tracking device. The method further includes operations for storing the motion data in memory, and for identifying one or more intervals during a day. Each interval includes a start time and an end time, and a near-end time is defined between the start and the end time. For each interval, the number of steps taken during the interval is determined, and the number of steps is compared against a goal defined by a number of steps to be taken during the interval. A first notification is displayed when the number of steps is less than the goal and the near-end time has been reached. A second notification is displayed congratulating the user if the interval goal is reached.

30 Claims, 21 Drawing Sheets

(51) Int. Cl.
| | |
|---|---|
| *G01C 22/00* | (2006.01) |
| *A61B 5/00* | (2006.01) |
| *A61B 5/11* | (2006.01) |
| *A61B 5/01* | (2006.01) |
| *A61B 5/021* | (2006.01) |
| *A61B 5/024* | (2006.01) |
| *A61B 5/0476* | (2006.01) |
| *A61B 5/0488* | (2006.01) |
| *A61B 5/053* | (2006.01) |
| *A61B 5/145* | (2006.01) |

(52) U.S. Cl.
 CPC .......... *A61B 5/1118* (2013.01); *A61B 5/6898* (2013.01); *A61B 5/742* (2013.01); *A61B 5/7405* (2013.01); *A61B 5/7435* (2013.01); *A61B 5/7455* (2013.01); *A61B 5/01* (2013.01); *A61B 5/021* (2013.01); *A61B 5/02405* (2013.01); *A61B 5/0476* (2013.01); *A61B 5/0488* (2013.01); *A61B 5/0531* (2013.01); *A61B 5/14532* (2013.01); *A61B 5/4809* (2013.01); *A61B 5/4815* (2013.01); *A61B 5/4848* (2013.01); *A61B 5/4866* (2013.01); *A61B 5/681* (2013.01); *A61B 5/744* (2013.01)

(58) Field of Classification Search
 USPC .......................... 600/300, 587, 595; 702/160
 See application file for complete search history.

(56) References Cited

U.S. PATENT DOCUMENTS

| | | | |
|---|---|---|---|
| 2,883,255 A | 4/1959 | Anderson | |
| 3,163,856 A | 12/1964 | Kirby | |
| 3,250,270 A | 5/1966 | Walter | |
| 3,522,383 A | 7/1970 | Chang | |
| 3,918,658 A | 11/1975 | Beller | |
| 4,192,000 A | 3/1980 | Lipsey | |
| 4,244,020 A | 1/1981 | Ratcliff | |
| 4,281,663 A | 8/1981 | Pringle | |
| 4,284,849 A | 8/1981 | Anderson et al. | |
| 4,312,358 A | 1/1982 | Barney | |
| 4,367,752 A | 1/1983 | Jimenez et al. | |
| 4,390,922 A | 6/1983 | Pelliccia | |
| 4,407,295 A | 10/1983 | Steuer et al. | |
| 4,425,921 A | 1/1984 | Fujisaki et al. | |
| 4,575,804 A | 3/1986 | Ratcliff | |
| 4,578,769 A | 3/1986 | Frederick | |
| 4,617,525 A | 10/1986 | Lloyd | |
| 4,855,942 A * | 8/1989 | Bianco .................. | A63B 24/00 235/105 |
| 4,887,249 A | 12/1989 | Thinesen | |
| 4,930,518 A | 6/1990 | Hrushesky | |
| 4,977,509 A | 12/1990 | Pitchford et al. | |
| 5,058,427 A | 10/1991 | Brandt | |
| 5,224,059 A | 6/1993 | Nitta et al. | |
| 5,295,085 A | 3/1994 | Hoffacker | |
| 5,314,389 A | 5/1994 | Dotan | |
| 5,323,650 A | 6/1994 | Fullen et al. | |
| 5,365,930 A | 11/1994 | Takashima et al. | |
| 5,446,705 A | 8/1995 | Haas et al. | |
| 5,456,648 A | 10/1995 | Edinburg et al. | |
| 5,485,402 A * | 1/1996 | Smith .................. | A61B 5/1038 340/870.01 |
| 5,553,296 A | 9/1996 | Forrest et al. | |
| 5,583,776 A | 12/1996 | Levi et al. | |
| 5,645,509 A | 7/1997 | Brewer et al. | |
| 5,671,162 A | 9/1997 | Werbin | |
| 5,704,350 A | 1/1998 | Williams, III | |
| 5,724,265 A | 3/1998 | Hutchings | |
| 5,817,008 A | 10/1998 | Rafert et al. | |
| 5,890,128 A | 3/1999 | Diaz et al. | |
| 5,891,042 A | 4/1999 | Sham et al. | |
| 5,894,454 A | 4/1999 | Kondo | |
| 5,899,963 A | 5/1999 | Hutchings | |
| 5,941,828 A | 8/1999 | Archibald et al. | |
| 5,947,868 A | 9/1999 | Dugan | |
| 5,955,667 A | 9/1999 | Fyfe | |
| 5,976,083 A | 11/1999 | Richardson et al. | |
| 6,018,705 A * | 1/2000 | Gaudet ................ | A61B 5/1121 235/105 |
| 6,077,193 A | 6/2000 | Buhler et al. | |
| 6,078,874 A | 6/2000 | Piety et al. | |
| 6,085,248 A | 7/2000 | Sambamurthy et al. | |
| 6,129,686 A | 10/2000 | Friedman | |
| 6,145,389 A * | 11/2000 | Ebeling ................ | G01C 22/006 73/865.4 |
| 6,183,425 B1 | 2/2001 | Whalen et al. | |
| 6,213,872 B1 * | 4/2001 | Harada .................. | A63B 24/00 235/105 |
| 6,241,684 B1 | 6/2001 | Amano et al. | |
| 6,287,262 B1 | 9/2001 | Amano et al. | |
| 6,301,964 B1 | 10/2001 | Fyfe et al. | |
| 6,302,789 B2 | 10/2001 | Harada et al. | |
| 6,305,221 B1 | 10/2001 | Hutchings | |
| 6,309,360 B1 | 10/2001 | Mault | |
| 6,469,639 B2 | 10/2002 | Tanenhaus et al. | |
| 6,478,736 B1 | 11/2002 | Mault | |
| 6,513,381 B2 | 2/2003 | Fyfe et al. | |
| 6,513,532 B2 | 2/2003 | Mault et al. | |
| 6,527,711 B1 | 3/2003 | Stivoric et al. | |
| 6,529,827 B1 | 3/2003 | Beason et al. | |
| 6,558,335 B1 | 5/2003 | Thede | |
| 6,561,951 B2 | 5/2003 | Cannon et al. | |
| 6,571,200 B1 | 5/2003 | Mault | |
| 6,585,622 B1 | 7/2003 | Shum et al. | |
| 6,607,493 B2 | 8/2003 | Song | |
| 6,620,078 B2 | 9/2003 | Pfeffer | |
| 6,678,629 B2 | 1/2004 | Tsuji | |
| 6,699,188 B2 | 3/2004 | Wessel | |
| 6,761,064 B2 | 7/2004 | Tsuji | |
| 6,772,331 B1 | 8/2004 | Hind et al. | |
| 6,790,178 B1 | 9/2004 | Mault et al. | |
| 6,808,473 B2 | 10/2004 | Hisano et al. | |
| 6,811,516 B1 | 11/2004 | Dugan | |
| 6,813,582 B2 | 11/2004 | Levi et al. | |
| 6,813,931 B2 | 11/2004 | Yadav et al. | |
| 6,856,938 B2 | 2/2005 | Kurtz | |
| 6,862,575 B1 | 3/2005 | Anttila et al. | |
| 7,041,032 B1 | 5/2006 | Calvano | |
| 7,062,225 B2 | 6/2006 | White | |
| 7,099,237 B2 | 8/2006 | Lall | |
| 7,133,690 B2 | 11/2006 | Ranta-Aho et al. | |
| 7,162,368 B2 | 1/2007 | Levi et al. | |
| 7,171,331 B2 | 1/2007 | Vock et al. | |
| 7,200,517 B2 | 4/2007 | Darley et al. | |
| 7,246,033 B1 | 7/2007 | Kudo | |
| 7,261,690 B2 | 8/2007 | Teller et al. | |
| 7,272,982 B2 | 9/2007 | Neuhauser et al. | |
| 7,285,090 B2 | 10/2007 | Stivoric et al. | |
| 7,373,820 B1 | 5/2008 | James | |
| 7,443,292 B2 | 10/2008 | Jensen et al. | |
| 7,457,724 B2 | 11/2008 | Vock et al. | |
| 7,467,060 B2 | 12/2008 | Kulach et al. | |
| 7,502,643 B2 | 3/2009 | Farringdon et al. | |
| 7,505,865 B2 | 3/2009 | Ohkubo et al. | |
| 7,539,532 B2 | 5/2009 | Tran | |
| 7,558,622 B2 | 7/2009 | Tran | |
| 7,559,877 B2 | 7/2009 | Parks et al. | |
| 7,608,050 B2 | 10/2009 | Shugg | |
| 7,640,134 B2 * | 12/2009 | Park ...................... | G01C 22/006 600/587 |
| 7,653,508 B1 | 1/2010 | Kahn et al. | |
| 7,690,556 B1 | 4/2010 | Kahn et al. | |
| 7,713,173 B2 | 5/2010 | Shin et al. | |
| 7,762,952 B2 | 7/2010 | Lee et al. | |
| 7,771,320 B2 | 8/2010 | Riley et al. | |
| 7,774,156 B2 | 8/2010 | Niva et al. | |
| 7,789,802 B2 | 9/2010 | Lee et al. | |
| 7,881,902 B1 | 2/2011 | Kahn et al. | |
| 7,927,253 B2 | 4/2011 | Vincent et al. | |
| 7,942,824 B1 | 5/2011 | Kayyali et al. | |
| 7,953,549 B2 | 5/2011 | Graham et al. | |

(56) References Cited

U.S. PATENT DOCUMENTS

| | | | |
|---|---|---|---|
| 7,959,539 B2* | 6/2011 | Takeishi | A63B 69/0028 377/24.2 |
| 7,983,876 B2 | 7/2011 | Vock et al. | |
| 8,005,922 B2 | 8/2011 | Boudreau et al. | |
| 8,028,443 B2 | 10/2011 | Case, Jr. | |
| 8,055,469 B2 | 11/2011 | Kulach et al. | |
| 8,099,318 B2 | 1/2012 | Moukas et al. | |
| 8,132,037 B2 | 3/2012 | Fehr et al. | |
| 8,172,761 B1 | 5/2012 | Rulkov et al. | |
| 8,177,260 B2 | 5/2012 | Tropper et al. | |
| 8,180,591 B2 | 5/2012 | Yuen et al. | |
| 8,180,592 B2 | 5/2012 | Yuen et al. | |
| 8,270,297 B2 | 9/2012 | Akasaka et al. | |
| 8,311,769 B2 | 11/2012 | Yuen et al. | |
| 8,311,770 B2 | 11/2012 | Yuen et al. | |
| 8,386,008 B2 | 2/2013 | Yuen et al. | |
| 8,437,980 B2 | 5/2013 | Yuen et al. | |
| 8,462,591 B1 | 6/2013 | Marhaben | |
| 8,463,576 B2 | 6/2013 | Yuen et al. | |
| 8,463,577 B2 | 6/2013 | Yuen et al. | |
| 8,487,771 B2 | 7/2013 | Hsieh et al. | |
| 8,533,269 B2 | 9/2013 | Brown | |
| 8,533,620 B2 | 9/2013 | Hoffman et al. | |
| 8,543,185 B2 | 9/2013 | Yuen et al. | |
| 8,543,351 B2 | 9/2013 | Yuen et al. | |
| 8,548,770 B2 | 10/2013 | Yuen et al. | |
| 8,562,489 B2 | 10/2013 | Burton et al. | |
| 8,583,402 B2 | 11/2013 | Yuen et al. | |
| 8,597,093 B2 | 12/2013 | Engelberg et al. | |
| 8,634,796 B2 | 1/2014 | Johnson | |
| 8,638,228 B2 | 1/2014 | Amigo et al. | |
| 8,670,953 B2 | 3/2014 | Yuen et al. | |
| 8,684,900 B2 | 4/2014 | Tran | |
| 8,690,578 B1 | 4/2014 | Nusbaum et al. | |
| 8,712,723 B1* | 4/2014 | Kahn | G01B 21/02 377/24.2 |
| 8,734,296 B1* | 5/2014 | Brumback | G06F 19/3406 482/8 |
| 8,738,321 B2 | 5/2014 | Yuen et al. | |
| 8,738,323 B2 | 5/2014 | Yuen et al. | |
| 8,738,925 B1* | 5/2014 | Park | H04B 7/26 380/270 |
| 8,744,803 B2 | 6/2014 | Park et al. | |
| 8,762,101 B2 | 6/2014 | Yuen et al. | |
| 8,764,651 B2 | 7/2014 | Tran | |
| 8,825,445 B2* | 9/2014 | Hoffman | A63B 24/0062 482/8 |
| 8,847,988 B2 | 9/2014 | Geisner et al. | |
| 8,849,610 B2* | 9/2014 | Molettiere | A61B 5/6838 702/160 |
| 8,868,377 B2 | 10/2014 | Yuen et al. | |
| 8,909,543 B2 | 12/2014 | Tropper et al. | |
| 8,949,070 B1 | 2/2015 | Kahn et al. | |
| 8,954,290 B2 | 2/2015 | Yuen et al. | |
| 8,961,414 B2 | 2/2015 | Teller et al. | |
| 8,968,195 B2 | 3/2015 | Tran | |
| 9,031,812 B2* | 5/2015 | Roberts | G08B 21/182 235/105 |
| 9,042,971 B2 | 5/2015 | Brumback et al. | |
| 9,047,648 B1 | 6/2015 | Lekutai et al. | |
| 9,062,976 B2* | 6/2015 | Tanabe | G01C 22/006 |
| 9,066,209 B2* | 6/2015 | Yuen | A61B 5/0002 |
| 9,288,298 B2* | 3/2016 | Choudhary | H04L 51/00 |
| 9,310,909 B2* | 4/2016 | Myers | A61B 5/0022 |
| 2001/0049470 A1 | 12/2001 | Mault et al. | |
| 2001/0055242 A1 | 12/2001 | Deshmuhk et al. | |
| 2002/0013717 A1 | 1/2002 | Ando et al. | |
| 2002/0019585 A1 | 2/2002 | Dickenson | |
| 2002/0077219 A1 | 6/2002 | Cohen et al. | |
| 2002/0082144 A1 | 6/2002 | Pfeffer | |
| 2002/0087264 A1 | 7/2002 | Hills et al. | |
| 2002/0109600 A1 | 8/2002 | Mault et al. | |
| 2002/0178060 A1 | 11/2002 | Sheehan | |
| 2002/0191797 A1 | 12/2002 | Perlman | |
| 2002/0198776 A1 | 12/2002 | Nara et al. | |
| 2003/0018523 A1 | 1/2003 | Rappaport et al. | |
| 2003/0050537 A1 | 3/2003 | Wessel | |
| 2003/0065561 A1 | 4/2003 | Brown et al. | |
| 2003/0131059 A1 | 7/2003 | Brown et al. | |
| 2003/0171189 A1 | 9/2003 | Kaufman | |
| 2003/0176815 A1* | 9/2003 | Baba | A61B 5/02438 600/595 |
| 2003/0208335 A1 | 11/2003 | Unuma et al. | |
| 2003/0226695 A1 | 12/2003 | Mault | |
| 2004/0054497 A1 | 3/2004 | Kurtz | |
| 2004/0061324 A1 | 4/2004 | Howard | |
| 2004/0116837 A1* | 6/2004 | Yamaguchi | A61B 5/02438 600/595 |
| 2004/0117963 A1 | 6/2004 | Schneider | |
| 2004/0122488 A1 | 6/2004 | Mazar et al. | |
| 2004/0152957 A1 | 8/2004 | Stivoric et al. | |
| 2004/0239497 A1 | 12/2004 | Schwartzman et al. | |
| 2004/0249299 A1 | 12/2004 | Cobb | |
| 2004/0257557 A1 | 12/2004 | Block | |
| 2005/0037844 A1 | 2/2005 | Shum et al. | |
| 2005/0038679 A1 | 2/2005 | Short | |
| 2005/0054938 A1 | 3/2005 | Wehman et al. | |
| 2005/0102172 A1 | 5/2005 | Sirmans, Jr. | |
| 2005/0107723 A1 | 5/2005 | Wehman et al. | |
| 2005/0163056 A1 | 7/2005 | Ranta-Aho et al. | |
| 2005/0171410 A1 | 8/2005 | Hjelt et al. | |
| 2005/0186965 A1 | 8/2005 | Pagonis et al. | |
| 2005/0187481 A1 | 8/2005 | Hatib | |
| 2005/0195830 A1 | 9/2005 | Chitrapu et al. | |
| 2005/0216724 A1 | 9/2005 | Isozaki et al. | |
| 2005/0228244 A1 | 10/2005 | Banet | |
| 2005/0228692 A1 | 10/2005 | Hodgdon | |
| 2005/0234742 A1 | 10/2005 | Hodgdon | |
| 2005/0248718 A1 | 11/2005 | Howell et al. | |
| 2005/0272564 A1 | 12/2005 | Pyles et al. | |
| 2006/0004265 A1 | 1/2006 | Pulkkinen et al. | |
| 2006/0020174 A1 | 1/2006 | Matsumura | |
| 2006/0020177 A1 | 1/2006 | Seo et al. | |
| 2006/0025282 A1 | 2/2006 | Redmann | |
| 2006/0039348 A1 | 2/2006 | Racz et al. | |
| 2006/0047208 A1 | 3/2006 | Yoon | |
| 2006/0047447 A1 | 3/2006 | Brady et al. | |
| 2006/0064276 A1* | 3/2006 | Ren | G01C 22/006 702/160 |
| 2006/0069619 A1 | 3/2006 | Walker et al. | |
| 2006/0089542 A1 | 4/2006 | Sands | |
| 2006/0111944 A1 | 5/2006 | Sirmans, Jr. | |
| 2006/0129436 A1 | 6/2006 | Short | |
| 2006/0143645 A1 | 6/2006 | Vock et al. | |
| 2006/0166718 A1 | 7/2006 | Seshadri et al. | |
| 2006/0217231 A1 | 9/2006 | Parks et al. | |
| 2006/0241521 A1* | 10/2006 | Cohen | A61B 5/0002 600/595 |
| 2006/0247952 A1 | 11/2006 | Muraca | |
| 2006/0277474 A1 | 12/2006 | Robarts et al. | |
| 2006/0282021 A1 | 12/2006 | DeVaul et al. | |
| 2006/0287883 A1 | 12/2006 | Turgiss et al. | |
| 2006/0288117 A1 | 12/2006 | Raveendran et al. | |
| 2007/0011028 A1 | 1/2007 | Sweeney | |
| 2007/0049384 A1 | 3/2007 | King et al. | |
| 2007/0050715 A1 | 3/2007 | Behar | |
| 2007/0051369 A1 | 3/2007 | Choi et al. | |
| 2007/0061593 A1 | 3/2007 | Celikkan et al. | |
| 2007/0071643 A1 | 3/2007 | Hall et al. | |
| 2007/0072156 A1 | 3/2007 | Kaufman et al. | |
| 2007/0083095 A1 | 4/2007 | Rippo et al. | |
| 2007/0083602 A1 | 4/2007 | Heggenhougen et al. | |
| 2007/0123391 A1 | 5/2007 | Shin et al. | |
| 2007/0135264 A1 | 6/2007 | Rosenberg | |
| 2007/0136093 A1 | 6/2007 | Rankin et al. | |
| 2007/0146116 A1 | 6/2007 | Kimbrell | |
| 2007/0155277 A1 | 7/2007 | Amitai et al. | |
| 2007/0159926 A1 | 7/2007 | Prstojevich et al. | |
| 2007/0179356 A1 | 8/2007 | Wessel | |
| 2007/0194066 A1 | 8/2007 | Ishihara et al. | |
| 2007/0197920 A1 | 8/2007 | Adams | |
| 2007/0208544 A1 | 9/2007 | Kulach et al. | |
| 2007/0276271 A1 | 11/2007 | Chan | |

(56) References Cited

U.S. PATENT DOCUMENTS

| | | |
|---|---|---|
| 2007/0288265 A1 | 12/2007 | Quinian et al. |
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katragadda et al. |
| 2008/0059113 A1* | 3/2008 | Tsubata ............... G01C 22/006 702/160 |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0114829 A1 | 5/2008 | Button et al. |
| 2008/0125288 A1 | 5/2008 | Case |
| 2008/0129457 A1 | 6/2008 | Ritter et al. |
| 2008/0134102 A1 | 6/2008 | Movold et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0172204 A1* | 7/2008 | Nagashima ............ G01C 22/006 702/160 |
| 2008/0176655 A1 | 7/2008 | James et al. |
| 2008/0243432 A1* | 10/2008 | Kato .................... G01C 22/006 702/160 |
| 2008/0275309 A1 | 11/2008 | Stivoric et al. |
| 2008/0287751 A1 | 11/2008 | Stivoric et al. |
| 2009/0018797 A1* | 1/2009 | Kasama ............... G01C 22/006 702/160 |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0054751 A1 | 2/2009 | Babashan et al. |
| 2009/0058635 A1 | 3/2009 | LaLonde et al. |
| 2009/0063193 A1 | 3/2009 | Barton et al. |
| 2009/0063293 A1 | 3/2009 | Mirrashidi et al. |
| 2009/0093341 A1 | 4/2009 | James et al. |
| 2009/0098821 A1 | 4/2009 | Shinya |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0299691 A1* | 12/2009 | Shimaoka ............ G01C 22/006 702/160 |
| 2009/0307517 A1 | 12/2009 | Fehr et al. |
| 2009/0309742 A1 | 12/2009 | Alexander et al. |
| 2010/0023348 A1 | 1/2010 | Hardee et al. |
| 2010/0056208 A1* | 3/2010 | Ashida ................ G01C 22/006 455/556.1 |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0079291 A1 | 4/2010 | Kroll et al. |
| 2010/0125729 A1 | 5/2010 | Baentsch et al. |
| 2010/0130873 A1 | 5/2010 | Yuen et al. |
| 2010/0158494 A1 | 6/2010 | King |
| 2010/0159709 A1 | 6/2010 | Kotani et al. |
| 2010/0167783 A1 | 7/2010 | Alameh et al. |
| 2010/0179411 A1 | 7/2010 | Holmström et al. |
| 2010/0185064 A1 | 7/2010 | Bandic et al. |
| 2010/0205541 A1 | 8/2010 | Rapaport et al. |
| 2010/0217099 A1 | 8/2010 | LeBoeuf et al. |
| 2010/0222179 A1 | 9/2010 | Temple et al. |
| 2010/0261987 A1 | 10/2010 | Kamath et al. |
| 2010/0262045 A1* | 10/2010 | Heaton ................ A61B 5/1112 600/595 |
| 2010/0292050 A1 | 11/2010 | DiBenedetto |
| 2010/0292600 A1 | 11/2010 | DiBenedetto et al. |
| 2010/0295684 A1 | 11/2010 | Hsieh et al. |
| 2010/0298656 A1 | 11/2010 | McCombie et al. |
| 2010/0298661 A1 | 11/2010 | McCombie et al. |
| 2010/0304674 A1 | 12/2010 | Kim et al. |
| 2010/0311544 A1 | 12/2010 | Robinette et al. |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0021143 A1 | 1/2011 | Kapur et al. |
| 2011/0022349 A1 | 1/2011 | Stirling et al. |
| 2011/0080349 A1 | 4/2011 | Holbein et al. |
| 2011/0087076 A1 | 4/2011 | Brynelsen et al. |
| 2011/0087137 A1* | 4/2011 | Hanoun ............... A61B 5/0205 600/587 |
| 2011/0106449 A1 | 5/2011 | Chowdhary et al. |
| 2011/0131005 A1* | 6/2011 | Ueshima ............ A63B 24/0062 702/141 |
| 2011/0145894 A1 | 6/2011 | Garcia Morchon et al. |
| 2011/0153773 A1 | 6/2011 | Vandwalle |
| 2011/0167262 A1 | 7/2011 | Ross et al. |
| 2011/0193704 A1 | 8/2011 | Harper et al. |
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2012/0015778 A1 | 1/2012 | Lee et al. |
| 2012/0035487 A1 | 2/2012 | Werner et al. |
| 2012/0046113 A1 | 2/2012 | Ballas |
| 2012/0072165 A1 | 3/2012 | Jallon |
| 2012/0083705 A1 | 4/2012 | Yuen et al. |
| 2012/0083714 A1* | 4/2012 | Yuen .................... A61B 5/0002 600/587 |
| 2012/0083715 A1 | 4/2012 | Yuen et al. |
| 2012/0083716 A1 | 4/2012 | Yuen et al. |
| 2012/0084053 A1* | 4/2012 | Yuen .................... A61B 5/0002 702/160 |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kääriäinen et al. |
| 2012/0116684 A1 | 5/2012 | Ingrassia, Jr. et al. |
| 2012/0119911 A1 | 5/2012 | Jeon et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0183939 A1 | 7/2012 | Aragones et al. |
| 2012/0203503 A1* | 8/2012 | Nakamura ............. G04G 21/02 702/160 |
| 2012/0215328 A1 | 8/2012 | Schmelzer |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0296400 A1 | 11/2012 | Bierman et al. |
| 2012/0297229 A1 | 11/2012 | Desai et al. |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1 | 5/2013 | Weast et al. |
| 2013/0132501 A1 | 5/2013 | Vandwalle et al. |
| 2013/0151196 A1 | 6/2013 | Yuen et al. |
| 2013/0158369 A1 | 6/2013 | Yuen et al. |

(56) References Cited

U.S. PATENT DOCUMENTS

| | | |
|---|---|---|
| 2013/0166048 A1 | 6/2013 | Werner et al. |
| 2013/0187789 A1 | 7/2013 | Lowe |
| 2013/0190008 A1 | 7/2013 | Vathsangam et al. |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2013/0331058 A1 | 12/2013 | Harvey |
| 2013/0337974 A1 | 12/2013 | Yanev et al. |
| 2013/0345978 A1 | 12/2013 | Lush et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0085077 A1 | 3/2014 | Luna et al. |
| 2014/0094941 A1 | 4/2014 | Ellis et al. |
| 2014/0121471 A1 | 5/2014 | Walker |
| 2014/0125618 A1 | 5/2014 | Panther et al. |
| 2014/0142466 A1* | 5/2014 | Kawabe .............. A61B 5/112 600/595 |
| 2014/0164611 A1 | 6/2014 | Molettiere et al. |
| 2014/0176475 A1 | 6/2014 | Myers |
| 2014/0180022 A1 | 6/2014 | Stivoric et al. |
| 2014/0188431 A1* | 7/2014 | Barfield .............. G01O 5/06 702/160 |
| 2014/0200691 A1* | 7/2014 | Lee .............. A61B 5/1118 700/91 |
| 2014/0207264 A1 | 7/2014 | Quy |
| 2014/0213858 A1 | 7/2014 | Presura et al. |
| 2014/0275885 A1 | 9/2014 | Isaacson et al. |
| 2014/0278229 A1 | 9/2014 | Hong et al. |
| 2014/0288435 A1 | 9/2014 | Richards |
| 2014/0316305 A1* | 10/2014 | Venkatraman ........ A61B 5/1112 600/595 |
| 2014/0337451 A1 | 11/2014 | Choudhary et al. |
| 2014/0337621 A1 | 11/2014 | Nakhimov |
| 2015/0026647 A1 | 1/2015 | Park et al. |
| 2015/0057967 A1 | 2/2015 | Albinali |
| 2015/0137994 A1 | 5/2015 | Rahman et al. |
| 2015/0141873 A1* | 5/2015 | Fei .............. A61B 5/112 600/595 |
| 2015/0198460 A1* | 7/2015 | Yamato .............. A61B 5/1118 702/160 |
| 2015/0220883 A1 | 8/2015 | B'far et al. |
| 2015/0289802 A1 | 10/2015 | Thomas et al. |
| 2015/0324541 A1 | 11/2015 | Cheung et al. |
| 2015/0374267 A1 | 12/2015 | Laughlin |
| 2016/0058331 A1* | 3/2016 | Keen .............. G06F 9/542 600/595 |
| 2016/0058372 A1 | 3/2016 | Raghuram et al. |
| 2016/0063888 A1 | 3/2016 | McCallum et al. |
| 2016/0089572 A1* | 3/2016 | Liu .............. G06K 9/00342 434/255 |
| 2016/0107646 A1 | 4/2016 | Kolisetty et al. |
| 2017/0239523 A1 | 8/2017 | Cheng et al. |
| 2017/0243056 A1 | 8/2017 | Cheng et al. |
| 2017/0243508 A1 | 8/2017 | Cheng et al. |

FOREIGN PATENT DOCUMENTS

| | | |
|---|---|---|
| CN | 103226647 | 7/2013 |
| JP | 11347021 A | 12/1999 |
| RU | 2178588 C1 | 1/2002 |
| WO | WO 2002011019 A1 | 2/2002 |
| WO | WO 2006055125 A1 | 5/2006 |
| WO | WO 2006090197 A1 | 8/2006 |
| WO | WO 2008038141 A2 | 4/2008 |
| WO | WO 2009042965 A1 | 4/2009 |
| WO | WO 2012061438 A2 | 5/2012 |
| WO | WO 12/170586 | 12/2012 |
| WO | WO 12/170924 | 12/2012 |
| WO | WO 12/171032 | 12/2012 |
| WO | WO 15/127067 | 8/2015 |
| WO | WO 16/003269 | 1/2016 |

OTHER PUBLICATIONS

Clifford et al., "Altimeter and Barometer System", Freescale Semiconductor Application Note AN1979, Rev. 3, Nov. 2006, 10 pages.

Fang et al, "Design of a Wireless Assisted Pedestrian Dead Reckoning System—The NavMote Experience", IEEE Transactions on Instrumentation and Measurement, vol. 54, No. 6, Dec. 2005, pp. 2342-2358.

Fitbit Inc., "Fitbit Automatically Tracks Your Fitness and Sleep" published online at web.archive.org/web/20080910224820/http://www.fitbit.com, downloaded Sep. 10, 2008, 1 page.

Godfrey et al., "Direct Measurement of Human Movement by Accelerometry", Medical Engineering & Physics, vol. 30, 2008, pp. 1364-1386 (22 pages).

Godha et al., "Foot Mounted Inertia System for Pedestrian Naviation", Measurement Science and Technology, vol. 19, No. 7, May 2008, pp. 1-9 (10 pages).

Intersema, "Using MS5534 for altimeters and barometers", Application Note AN501, Jan. 2006, 12pages.

Ladetto et al, "On Foot Navigation: When GPS alone is not Enough", Journal of Navigation, vol. 53, No. 2, Sep. 2000, pp. 279-285 (6 pages).

Lammel et al., "Indoor Navigation with MEMS Sensors", Proceedings of the Eurosensors XIII conference, vol. 1, No. 1, Sep. 2009, pp. 532-535 (4 pages).

Lester et al, "Validated caloric expenditure estimation using a single body-worn sensor", Proc. of the Int'l Conf. on Ubiquitous Computing, 2009, pp. 225-234 (10 pages).

Lester et al., "A Hybrid Discriminative/Generative Approach for Modeling Human Activities", Proc. of the Int'l Joint Conf. Artificial Intelligence, 2005, pp. 766-772 (7 pages).

Ohtaki et al, "Automatic classification of ambulatory movements and evaluation of energy consumptions utilizing accelerometers and barometer", Microsystem Technologies, vol. 11, No. 8-10, Aug. 2005, pp. 1034-1040 (7 pages).

Parkka, et al, Activity Classification Using Realistic Data From Wearable Sensors, IEEE Transactions on Information Technology in Biomedicine, vol. 10, No. 1, Jan. 2006, pp. 119-128 (10pages).

PCT/IB07/03617 International Search Report dated Aug. 15, 2008, in related application, 3 pages.

Perrin et al, "Improvement of Walking Speed Prediction by Accelerometry and Altimetry, Validated by Satellite Positioning", Medical & Biological Engineering & Computing, vol. 38, 2000, pp. 164-168 (5 pages).

Retscher, "An Intelligent Multi-Sensor system for Pedestrian Navigation", Journal of Global Positioning Systems, vol. 5, No. 1, 2006, pp. 110-118 (9 pages).

Sagawa et al, "Classification of Human Moving Patterns Using Air Pressure and Acceleration", Proceedings of the 24th Annual Conference of the IEEE Industrial Electronics Society, vol. 2, Aug.-Sep. 1998, pp. 1214-1219 (6 pages).

(56) References Cited

OTHER PUBLICATIONS

Sagawa et al, "Non-restricted measurement of walking distance", IEEE Int'l Conf. on Systems, Man, and Cybernetics, vol. 3, Oct. 2000, pp. 1847-1852 (6 pages).
Specification of the Bluetooth® System, Core Package, version 4.1, Dec. 2013, vol. 0 & 1, 282 pages.
Stirling et al., "Evaluation of a New Method of Heading Estimation of Pedestrian Dead Reckoning Using Shoe Mounted Sensors", Journal of Navigation, vol. 58, 2005, pp. 31-45 (15 pages).
Suunto Lumi, "User Guide", Copyright Jun. and Sep. 2007, 49 pages.
Tanigawa et al, "Drift-Free Dynamic Height Sensor Using MEMS IMU Aided by MEMS Pressure Sensor", Workshop on Positioning, Navigation and Communication, Mar. 2008, pp. 191-196 (6 pages).
VTI Technologies, "SCP 1000-D01/D11 Pressure Sensor as Barometer and Altimeter", Application Note 33, Jun. 2006, 3 pages.
Lee, Mar. 3, 2017, Jawbone gets 2 patents nixed in Fitbit infringement suit, Law360, retrieved from https:///ww.law360.com/articles/898111,jawbone-gets-2-patents-nixed-in-fitbit-infringement-suit, 9 pp.

* cited by examiner

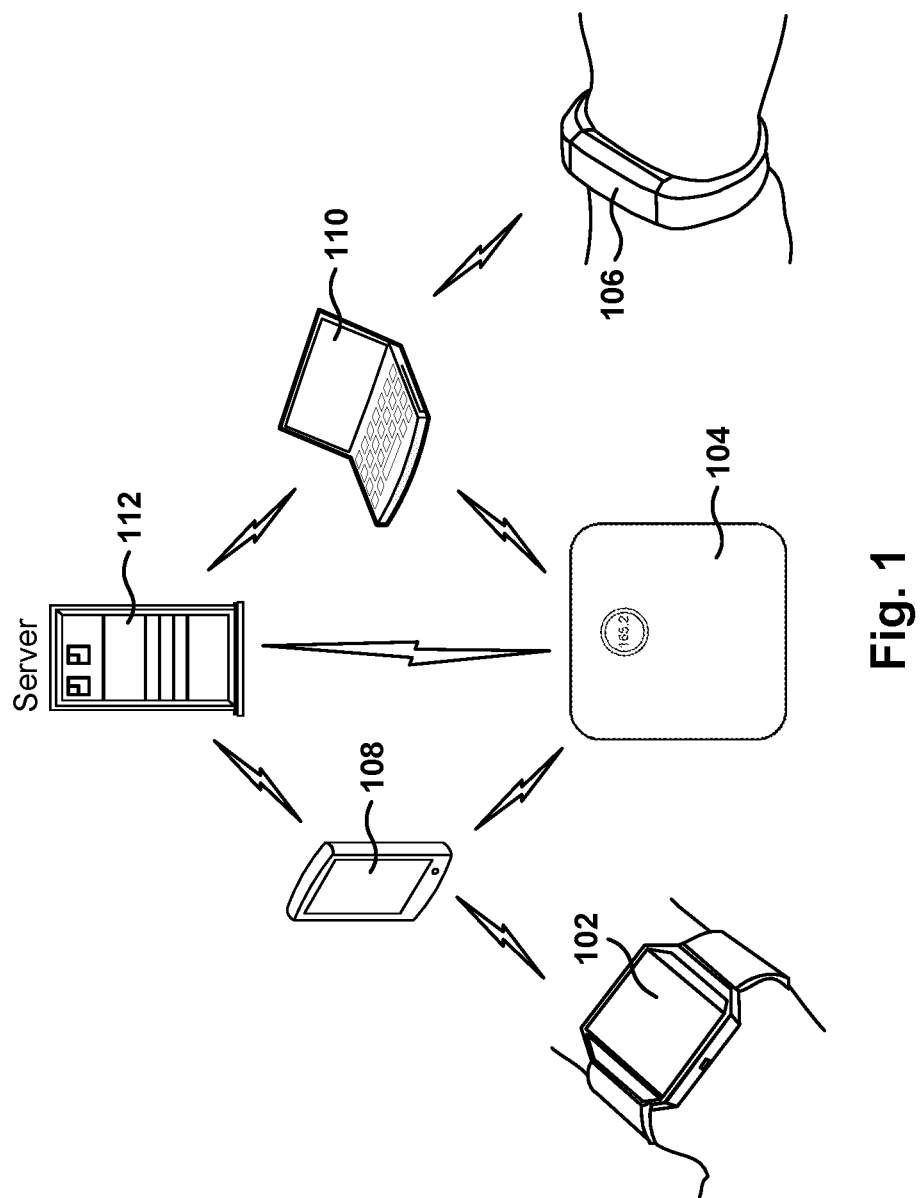

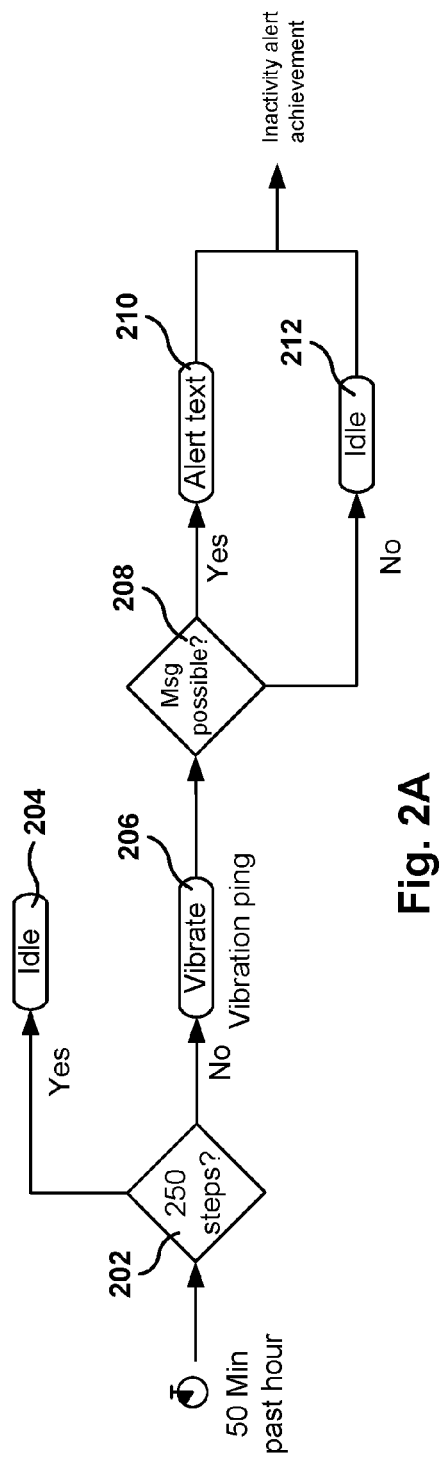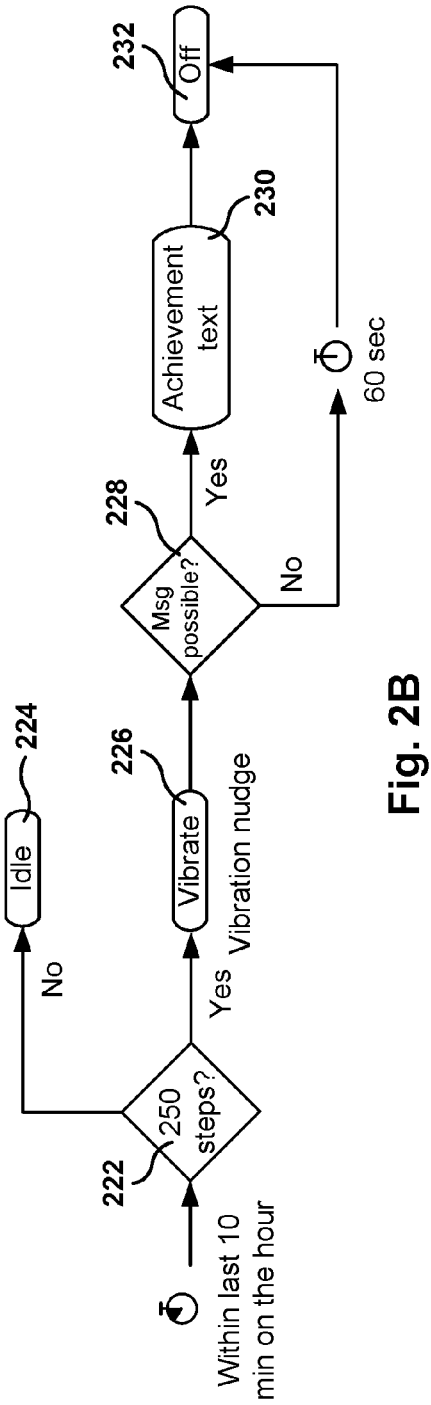
Fig. 2A
Fig. 2B

PERIODIC INACTIVITY ALERTS AND ACHIEVEMENT MESSAGES

CROSS REFERENCE TO RELATED APPLICATIONS

This application is related by subject matter to: U.S. patent application Ser. No. 15/048,965 filed on Feb. 19, 2016 and entitled "GENERATION OF SEDENTARY TIME INFORMATION BY ACTIVITY TRACKING DEVICE;" U.S. patent application Ser. No. 15/048,972 filed on Feb. 19, 2016 and entitled "TEMPORARY SUSPENSION OF INACTIVITY ALERTS IN ACTIVITY TRACKING DEVICE;" and U.S. patent application Ser. No. 15/048,976 filed on Feb. 19, 2016 and entitled "LIVE PRESENTATION OF DETAILED ACTIVITY CAPTURED BY ACTIVITY TRACKING DEVICE," all of which are incorporated herein by reference.

FIELD OF THE INVENTION

The present embodiments relate to methods, systems, and programs for tracking user motion activity, and more particularly, methods, systems, and computer programs for communicating information to enable reduction of sedentary time by users.

BACKGROUND

Description of the Related Art

The use of portable activity tracking devices has grown increasingly popular for people that want a way to track their activity levels throughout the day to accomplish fitness goals. Oftentimes, activity tracking devices, also referred to as trackers, report the number of steps taken by the person wearing the tracking device throughout the day, with the idea that the more steps taken, the higher the activity level, the better level of fitness will be achieved.

However, recent scientific studies have discovered that long periods of inactivity (e.g., sedentary times) may be bad for a person's health, even if that person is able to include regular exercise in their daily routine.

SUMMARY

Methods, devices, systems, and computer programs are presented for generating alarms and congratulatory messages to influence reductions in sedentary time. It should be appreciated that the present embodiments can be implemented in numerous ways, such as a method, an apparatus, a system, a device, or a computer program on a computer readable medium. Several embodiments are described below.

One general aspect includes a method, which includes an operation for capturing motion data using an activity tracking device when worn by a user. The method also includes an operation for storing the motion data to memory of the activity tracking device. The method also includes identifying one or more intervals of time during a day, each interval including a start time and an end time, a near-end time being defined between the start time and the end time. For each of the intervals, the method determines from the motion data a number of steps taken by the user during the interval, comparing the number of steps taken by the user against a goal defined by a predetermined number of steps to be taken by the user during the interval, and generating a first notification for display on the activity tracking device during the interval when the number of steps taken by the user is less than the goal and the near-end time of the interval has been reached.

One general aspect includes a method, which includes an operation for capturing motion data using an activity tracking device when worn by a user, and an operation for storing the motion data to memory of the activity tracking device. The method also includes identifying an interval of time having a start time and an end time, where a near-end time is defined between the start time and the end time. The method also includes determining from the motion data a number of steps taken by the user during the interval. The method also includes comparing the number of steps taken by the user against a goal defined by a predetermined number of steps to be taken by the user during the interval. The method also includes generating a first notification for display on the activity tracking before the end time when the number of steps taken by the user is less than the goal and the near-end time of the interval has been reached.

One general aspect includes a non-transitory computer-readable storage medium storing a computer program. The computer-readable storage medium includes program instructions for capturing motion data using an activity tracking device when worn by a user. The storage medium also includes program instructions for storing the motion data to memory of the activity tracking device. The storage medium also includes program instructions for identifying one or more intervals of time during a day, each interval including a start time and an end time, a near-end time being defined between the start time and the end time. The storage medium also includes, for each of the intervals, program instructions for determining from the motion data a number of steps taken by the user during the interval, program instructions for comparing the number of steps taken by the user against a goal defined by a predetermined number of steps to be taken by the user during the interval, and program instructions for generating a first notification for display on the activity tracking device during the interval when the number of steps taken by the user is less than the goal and the near-end time of the interval has been reached.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

FIG. 1 is a block diagram of a system architecture according to one embodiment.

FIG. 2A is a flowchart of a method for triggering inactivity alerts, according to one embodiment.

FIG. 2B is a flowchart of a method for generating achievement congratulatory messages, according to one embodiment.

FIGS. 7A-7E illustrate configuration screens of the GUI, according to one embodiment.

DETAILED DESCRIPTION

Figure 3A:
FIGS. 3A-3I show activity-related messages shown on the activity tracking device, according to one embodiment.

Methods, devices, systems, and computer programs are presented for generating alarms and congratulatory messages to influence users to reduce sedentary time. It will be apparent, that the present embodiments may be practiced without some or all of these specific details. In other instances, well-known process operations have not been described in detail in order not to unnecessarily obscure the present embodiments.

Embodiments presented herein periodically analyze user activity to encourage the user to avoid being inactive for long periods of time. Typically, users may only look at a daily goal (e.g., 10,000 steps) and do not pay much attention to activity levels throughout the day. Thus, a user may accomplish the daily goal but have large sedentary periods during the day. One way to avoid long sedentary periods is to monitor user activity in smaller intervals than a day, such as an hour, and then check if the user meets hourly goals. This way, the user is encouraged to meet the smaller hourly goals and avoid staying still for long periods.

Simple idle or sedentary alerts (e.g., "you haven't moved for one hour and 45 minutes) may provide a simple way for alerting a user to get up and move around, which may come with some health benefits. However, these "simple" sedentary alerts provide little information to the user, lack well-defined goals, and may generate alerts at inconvenient times for the user. Such downsides may have a negative effect on user engagement and motivation.

Recent studies suggest that regular activity breaks are more effective than continuous physical activity at decreasing postprandial glycemia and insulinemia in healthy, normal-weight adults. This proves the importance of avoiding prolonged uninterrupted periods of sedentary time.

Embodiments presented herein provide for the definition of sedentary-related goals and the tracking of activity throughout the day in order to reduce the amount of sedentary time of the user. In one embodiment, the period of time during which the activity is tracked during a day may vary, and can be user defined. Users enjoy positive reminders to walk around, or do some other exercise, throughout the day even though users may have already exercised that day. Further, the awareness of being sedentary for long stretches of time is important as users may overlook how much time users sit throughout the day. In addition, ongoing achievements throughout the day are compensated with motivating messages for an improved user experience.

What is needed is a way to motivate and inform users regarding their sedentary times in order to reduce sedentary times for a better fitness level. It is in this context that embodiments arise.

FIG. 1 is a block diagram of a system architecture according to one embodiment. Portable biometric devices, also referred to as activity tracking devices, will be referred to herein by way of example to illustrate aspects of the embodiments. Some activity tracking devices are portable and have shapes and sizes that are adapted to couple to the body of a user (e.g., activity tracking devices 102, 106), while other devices are carried by the user (e.g., mobile phone 108, laptop 110, tablet), and other devices may be stationary (e.g., electronic scale 104, a digital thermometer, personal computer).

The devices collect one or more types of physiological or environmental data from embedded sensors or external devices. The devices can then communicate the data to other devices, to one or more servers 112, or to other internet-viewable sources. As one example, while the user is wearing an activity tracking device 102, the device can calculate and store the number of steps taken by the user (the user's step count) from data collected by embedded sensors. Data representing the user's step count is then transmitted to an account on a web service (such as www.fitbit.com for example) where the data may be stored, processed, and viewed by the user. Indeed, the device may measure or calculate a plurality of other physiological metrics in addition to, or in place of, the user's step count.

These metrics include, but are not limited to, energy expenditure (e.g., calorie burn), floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (e.g., clock time), sleep phases, sleep quality, and/or sleep duration, and respiration rate. The device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field.

As used herein, the term "sync" refers to the action of exchanging data between a first device and a second device to update the second device with new information available to the first device that is not yet available to the second device. Additionally, "sync" may also refer to the exchange of information between two devices to provide updates to one of the devices with information available to the other device, or to coordinate information that is available, overlapping, or redundant in both devices. "Sync" may also be used in reference to sending and/or receiving data to and/or from another computing device or electronic storage devices including, but not limited to, a personal computer, a cloud based server, and a database. In some embodiments, a sync from one electronic device to another may occur through the use of one or more intermediary electronic devices. For example, data from an activity tracking device may be transmitted to a smart phone that forwards the data to a server.

Inactivity alerts are message presented to the user carrying activity information regarding sedentary times. The inactivity alerts are designed to trigger the wearer to get up and move around to break up long sedentary periods, and to give the wearer positive reinforcement when the wearer responds to the inactivity alert. In some embodiments, the alerts may also identify an amount of activity achieved.

In one embodiment, a sedentary time is a continuous period of time where the user has not reached an activity threshold to be considered active. In some embodiments, a sedentary time may represent a collection of two or more continuous periods of time where the user has not reached the activity threshold to be considered active. In one embodiment, the activity threshold is defined as a number of steps taken within the sedentary period of time (e.g., 20 steps). For example, a user is considered to be sedentary, or inactive, if the user has not walked at least 20 steps since the last active period ended, and if the user has walked 20 or more steps, the user is considered no longer sedentary and is now considered active. In some embodiments, a user is considered sedentary if the user has not walked the required number of steps within a predetermined period (e.g., 5 minutes, or 15 minutes, but other values are also possible). Once the user is considered sedentary, the timer for the sedentary time is started, and the sedentary time will end once the user becomes active again.

In another embodiment, the metabolic equivalent of task (MET) measurement is used to determine if the user is sedentary or active. The MET is a physiological measure expressing an energy cost of physical activity, and the MET is defined as the ratio of metabolic rate (related to the rate of energy consumption) to a reference metabolic rate.

In general, MET values range from 0.9 (while sleeping) to approximately 23 (while running at a 4 mile pace for a young healthy individual). The MET can be thought of as an index of the intensity of activities. For example, a MET measure for an inactive or asleep status is close to 1.0, a MET measure for a user walking is generally above 2.0, and a MET measure for a user swimming is between 10.0 and 11.0. While in some embodiments the sensor information obtains MET measurements, alternative embodiments may use more or different measurements (e.g., a number of steps, number of stairs climbed, number of turns of a bicycle pedal, etc.) indicative of the motion of the user wearing the wearable electronic device and/or heart rate measures indicative of the heart rate of the user. The term "heart rate monitor" may be used to refer to both a set of one or more sensors that generate heart sensor data indicative of a heart rate of a user and the calculation of the heart rate measures of the user.

MET is used as a means of expressing the intensity and energy expenditure of activities in a way comparable among persons of different weight. Actual energy expenditure (e.g., in calories or joules) during an activity depends on the person's body mass; therefore, the energy cost of the same activity will be different for persons of different weight.

In one embodiment, a person is considered active when the MET exceeds a value of 2, but other threshold values are also possible. Thus, the user is determined to be sedentary when the MET is below the predetermined MET threshold (e.g., 2) and the user is determined to be active when the MET is above, or at, the predetermined MET threshold.

FIG. 2A is a flowchart of a method for triggering inactivity alerts, according to one embodiment. In one embodiment, the day (or part of the day) is divided into blocks of time, also referred to as intervals, and a goal is set for each of the blocks of time or intervals. Embodiments described herein are described with reference to hourly blocks of time and hourly goals, but other embodiments may use the same principle with other blocks of time, such as blocks of 30 minutes, two hours, three hours, etc. The goal for each hour is referred to as the hourly goal or interval goal, e.g., walk 250 steps within each hour. For simplicity purposes, each hour associated with an hourly goal begins at a time of the day with a 0 minute offset, e.g., 9 o'clock, 10 o'clock, etc., but other embodiments may be defined with a schedule where the hours begin at a different offset of time with reference to the time clock.

In one embodiment, an inactivity alert is generated when a threshold time within the hour has been reached and the hourly goal has not been reached. For example, in one embodiment, the inactivity alert is generated after 50 minutes past the hour if the user has not walked 250 steps yet during those 50 minutes. The threshold time within the interval is also referred to as the near-end time. Thus, each hour associated with an hourly goal has a start time, an end time, and a near-end time between the start time and the end time. In one embodiment, the near-end time is 50 minutes past the hour, but in other embodiments, the near-end time is in the range of 30 minutes to 1 minute before the end time.

In other embodiments, the near-end time may be variable, and can be adjusted depending on how far the user is from reaching the hourly goal. For example, if the user only needs five more steps to reach the goal, the inactivity alert may be postponed five minutes to give the user the chance to walk those five steps.

Further, the goal for the number of hourly steps is configurable. For example, the user may start with an hourly goal of 250 steps and later increase or decrease that number.

Referring to the exemplary flowchart of FIG. 2A, when the near-end time is reached, a check is made in operation 202 to determine if the hourly goal (e.g., 250 steps) has been met. If the hourly goal has been met the method flows to operation 204, where no action is taken, e.g., the inactivity alert trigger is idle. If the hourly goal has not been met, the method flows to operation 206, where an inactivity alert is triggered in the form of a vibration of the activity tracking device, or using some other notification, such as a sound beep, or a combination of a vibration and a sound. In some embodiments, the notifications may be color coded, and may be presented with graphics representing activity or lack of activity, including numeric values.

From operation 206, the method flows to operation 208 where a check is made to determine if messaging is possible (e.g., enabled on the device) or if the device is on. If the result of the check is positive, the method flows to operation 210 where an inactivity alert in the form of a message (see "alert text" in FIG. 2A) is presented on the display, and if the result is negative, the inactivity alert in the form of a message is not triggered 212.

From operation 210 or operation 212, the method flows to the inactivity alert achievement flowchart discussed below with reference to FIG. 2B. It is noted that if the inactivity alert is not triggered in operation 202, then the inactivity alert achievement flowchart is not invoked, or in other words, if the user has met the hourly goal when the near-end time is reached, then a congratulatory message (which is described in more detail below in connection with FIG. 2B) will not be displayed.

In one embodiment, if the user has not met the hourly goal when the near-end time is reached but the user responds within the remaining time of the interval to meet the goal, then the user gets a congratulatory message, but the user only gets the congratulatory message if the user previously received the inactivity alert (as described above in connection with FIG. 2A). This way, a negative message regarding the failure to reach the goal, becomes a positive experience when the congratulatory message is received.

Further, based on behavioral change models, it is easier to change by defining and meeting small goals, instead of going for a hefty goal that may be difficult or impossible to achieve, resulting in a feeling of failure. By meeting small goals, the user gets a feeling of accomplishment.

In some embodiments, there are other conditions that must be met before generating the inactivity alert. For example, if the user starts an exercise (e.g., swimming, yoga), the inactivity alert is suspended. Also, if the user is sleeping or not wearing the activity tracking device, the inactivity alert is not generated. This means, that in order to generate the inactivity alert, the user must be wearing the activity tracking device and be awake.

Further, if the user configures the activity tracking device to cancel all alerts (e.g., "Do not disturb"), the inactivity alerts will not be presented. Also, if the user configures the activity tracking device to temporarily suspend inactivity alerts, the inactivity alerts will not be generated. More details are provided below with reference to FIG. 9C for placing on hold the generation of inactivity alerts.

FIG. 2B is a flowchart of a method for generating achievement congratulatory messages, according to one embodiment. While the various operations in this flowchart are presented and described sequentially, one of ordinary skill will appreciate that some or all of the operations may be executed in a different order, be combined or omitted, or be executed in parallel.

In some embodiments, if the user hits the hourly goal after receiving the inactivity alert, the user receives a celebratory alert, also referred to as congratulatory alert or message or a reward alert or message. For example, if the user reaches 250 steps before the hour expires, the user gets a congratulatory message.

In operation 222, the activity tracking device continues checking for reaching the interval goal (e.g., 250 steps) during the remaining time of the current interval. If the goal is not reached by the end of the current interval, the method flows to operation 224 where no action is taken. However, if the goal is reached during the remaining time of the current interval, the method flows to operation 226 where a vibration is generated. In one embodiment, the vibration of operations 206 (in FIG. 2A) and operation 226 follow the same pattern, but in other embodiments, the vibration pattern of operation 206 is different from the vibration pattern of operation 226.

From operation 226, the method flows to operation 228 to check if messaging is possible in the activity tracking device. If messaging is possible, the method flows to operation 230 where a congratulatory message (see "achievement text" in FIG. 2B) is presented to the user. If messaging is not possible, the activity tracking device continues checking for 60 seconds to determine if messaging is possible. After the 60 seconds, the method ends and the congratulatory message is not presented.

In other solutions, alerts are generated based on the amount of time that the user has been inactive, but those alerts can come at any random time and/or at an unexpected or inopportune time. However, presenting the inactivity alerts at expected times (such as the near-end times described herein), which can be configured or throttled by the user, provides a more positive and satisfying experience.

FIGS. 3A-3I show activity-related messages shown on the activity tracking device, according to one embodiment. In some interfaces, each interval (e.g., hour) is represented by a circle or other object, and the circles representing multiple intervals are arranged in an arc or a line. Each circle changes appearance (e.g., is filled with a specific color such as red) if the user reaches the hourly step goal for that hour (e.g., took over 250 steps that hour). Based on the progress, different text strings are shown below the visualizations. In some embodiments, when every hour goal (e.g., for a day) is met, the circles corresponding to all the hours change appearance (e.g., turn green) and the arc or line is connected to show the achievement of completing all the hourly goals. Also, in some embodiments, the circles are replaced with stars. In some embodiments, when the interval goal or a daily goal (as described in more detail below) is met, the congratulatory message includes an animation.

Most people have activities that are tied to the hour, so using hourly intervals is more successful for a higher percentage of people, because of the predictability of the inactivity alerts tied to the specific time on the hour.

FIG. 3A shows a user interface that includes a message about the number of steps left within the current hour to reach the goal. The interface includes an icon (e.g., a person) surrounded by a circle and the text message below.

The circle is used to show how much of the goal has been met within the hour, where the circle may have two different types of shading, or color, or any other distinctive visual clue to differentiate between percentage of goal accomplished and percentage of amount left to reach the goal. In FIG. 3A, the user has not taken any steps yet within the current hour, therefore, there's only one shading in the circle signifying that 0% has been accomplished.

Figure 3B:
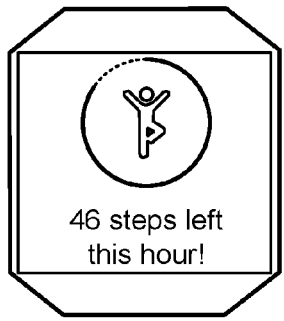

FIG. 3B shows another interface when the user has walked 204 steps within the current hour. The message states that 46 steps are left to meet the goal (e.g., "46 steps left this hour!"). The circle is "filled" by the respective percentage (about 80%) and the remainder (about 20%) is not filled to visually indicate how much is left to meet the goal. In one embodiment, as the user walks, the count of the steps remaining changes in real time.

Figure 3C:
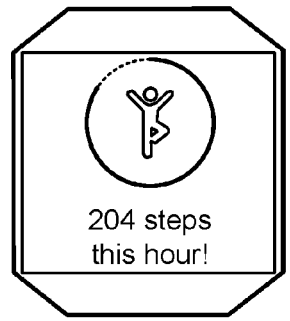

FIG. 3C shows the number of steps walked this hour instead of the number of steps left, as shown in FIG. 3B. Thus, FIG. 3C includes a text message stating the number of steps taken this hour, "204 steps this hour!" The circle is filled the same amount as in FIG. 3B as the number of steps left to reach the goal is the same. In one embodiment, as the user walks, the count of the steps taken this hour is updated in real time. In some embodiments, the interfaces displayed in FIGS. 3A-3C may correspond to the inactivity alerts described herein.

Figure 3D:

FIG. 3D illustrates a congratulatory message shown when the user reaches the hourly goal. In one embodiment, the icon changes color (e.g., the icon of the person is solid green instead of white with a black outline), the circle also changes format (e.g., the circle is completely filled in a different shade of green than the icon), and the text message indicates that the goal has been reached (e.g., "You hit 250!").

In one embodiment, a daily goal is also defined, as described in more detail below with reference to FIG. 5A.

The daily goal is a goal defined for a day indicating the minimum number of intervals of the day where the interval goal is met. For example, the daily goal may be 9 out of 9, or 7 of 9, or 6 out of 7, etc. In some embodiments, the daily goal requires that the user reaches the interval goal in all the intervals defined for the day, however, in other embodiments the daily goal does not require that the interval goal is met in all the intervals.

Figure 3E:
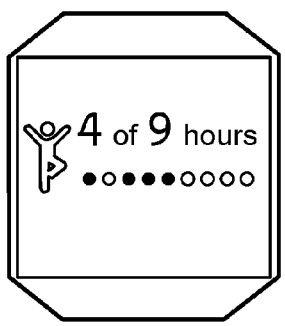

FIG. 3E shows a graphical user interface indicating the progress towards the daily goal. In the exemplary embodiment, the interface includes an icon (e.g., person), a text message indicating the progress towards the daily goal (e.g., 4 of 9 hours), and a plurality of the small circles in a line, where each circle represents an interval. The circles in the line may have at least two different shadings, a first shading indicating that the interval goal for the corresponding interval was reached, and a second shading indicating when the interval goal for the corresponding interval was not reached. In some embodiments, a third shading is provided to indicate the intervals in a future time.

Figure 3F:
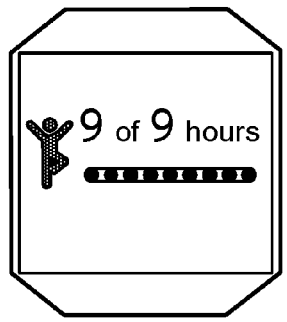

FIG. 3F shows the interface presented after the daily goal has been reached. Compared to the interface in FIG. 3E, the icon has changed format (e.g., changed color), the message shows the daily goal has been reached (e.g., "9 of 9 hours"), and the circles are all filled to indicate that the interval goal was reached. In addition, a line has been added to join all the circles, to further emphasize that the daily goal has been reached.

Figure 3G:
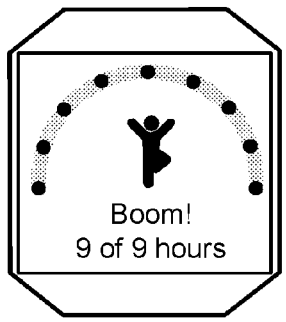

FIG. 3G shows another interface indicating that the daily goal has been reached. The icon is also filled in a different color, the circles are all filled but the circles are disposed on an arc, and a half-circle has been added to connect all the interval circles.

Figure 3H:
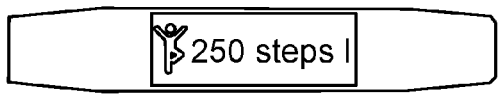
Figure 3I:

FIGS. 3H and 3I show the user interface for an activity tracking device with a smaller display. In one embodiment, text messages are scrolled through the display if the text messages are too long to be shown in their entirety. FIG. 3H shows an interface indicating how many steps left to meet the hourly goal (similar to the message of FIG. 3A). An icon is presented, where the icon is used to identify the message as a message associated with the inactivity alerts. The text message that scrolls through the display describes how many steps are left (e.g., "250 steps left this hour!"). FIG. 3I is an interface with a congratulatory message after the user completes the hourly goal.

As discussed above, some of the messages are accompanied by a vibration to call the user's attention towards meeting the hourly goal or the satisfaction of the hourly goal. Some activity trackers do not include a display, therefore, the activity alerts and messages may be displayed on a mobile device that is in communication with the activity tracker.

It is noted that the embodiments illustrated in FIGS. 3A-3I are exemplary. Other embodiments may utilize different interfaces, messages, icons, layouts, etc. The embodiments illustrated in FIGS. 3A-3I should therefore not be interpreted to be exclusive or limiting, but rather exemplary or illustrative.

Figures 4A, 4B, 4C:
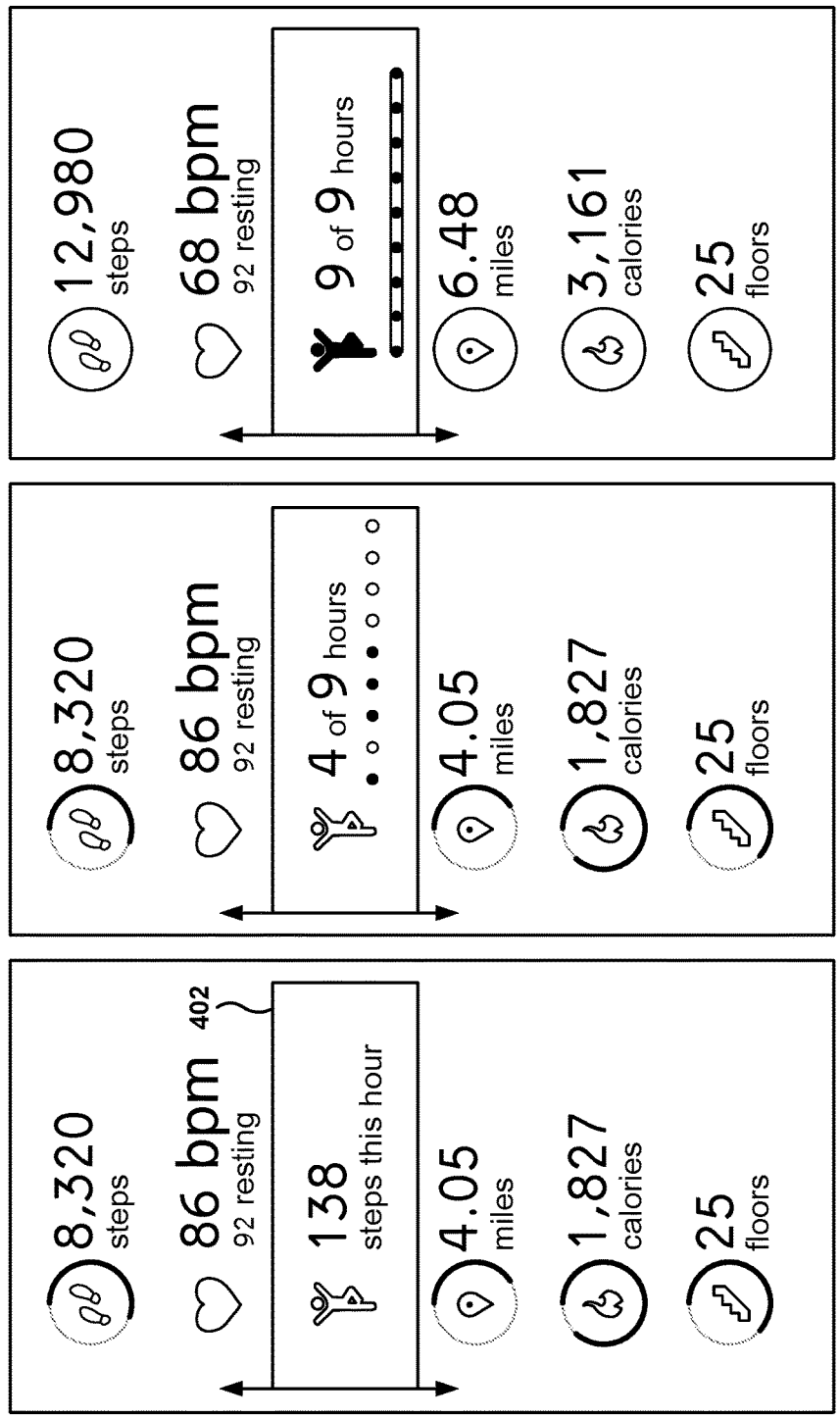
FIGS. 4A-4C illustrate the graphical user interface (GUI) presented on the activity tracking device, according to one embodiment.

FIGS. 4A-4C illustrate the graphical user interface (GUI) presented on the activity tracking device, according to one embodiment. In one embodiment, the tracking device includes a button and as the user presses the button, a different area of information is displayed. FIG. 4A illustrates the different messages presented, where only one of those is viewable at a time, as represented by sliding window 402.

Each of the messages includes a graphic icon that identifies the area of information. For example, two footsteps within a circle represents the number of daily steps, heart icon represents the heart rate, etc. Regarding hourly goals, the information includes an icon for hourly goals (e.g., a silhouette of a person with her arms up in the air and one bent knee) followed by information regarding the hourly goals.

As discussed above with reference to FIGS. 3A-3I, the hourly-goal information may include the number of steps taken this hour, the number of steps left to meet the hourly goal, etc. In addition, the hourly goal section may also include information regarding the daily goal for intervals where the hourly goal was met. Thus, FIG. 4B shows a message indicating that in 4 of 9 hours the hourly goal has been met. Additionally, a circle for each hourly goal may also be included to describe in which intervals the hourly goal was met (e.g., where each circle is filled with a specific color to indicate that the corresponding hourly goal was met). Accordingly, in some embodiments, if the user has not met the current hourly goal, then information including the number of steps taken this hour and/or the number of steps left to meet the hourly goal may be displayed (e.g., see FIG. 4A), whereas if the user has met the current hourly goal, information describing whether or not the hourly goal has been met for various intervals throughout the day may be displayed (e.g., see FIGS. 4B and 4C).

In FIG. 4C, a congratulatory message is displayed, where the icon for hourly goal information has a different color (e.g., filled with black color as illustrated in FIG. 4C, or changed from a red color to a green color, etc.), all the circles have been filled, and a line has been added to connect all the circles. In some embodiments, the circles in FIG. 4C may be filled in with a different color than the color used to fill the circles in FIG. 4B to indicate when each hourly goal was met. For example, the circles in FIG. 4B may change color from grey to red to indicate that the corresponding hourly goal was met, whereas the all the circles in FIG. 4C may be filled with the color green (and may be connected via a green line) to indicate that all the hourly goals and/or a daily goal has been met.

In some embodiments, the hourly-goal messages change to avoid monotony and to make the experience more interesting. In one embodiment, there is a plurality of inactivity alert messages (e.g., 15 messages) and a plurality of congratulatory messages (e.g., 20 messages). Therefore, the messages are selected at random, or following a linear order, or with some other selection criteria, to provide variety.

In one embodiment, a certain degree of randomness is combined with logic for selecting the messages. For example, the first three messages presented to the user for the inactivity alert include specific information (e.g., number of steps left to reach the goal), and the remainder of the messages include motivational information, but not necessarily the step count.

In one embodiment, the messages are defined as follows:

TABLE 1

| # | Order of Messages | Inactivity Messages | Congratulatory messages |
|---|---|---|---|
| 1 | #1 | <n> steps left this hour! | You hit 250! |
| 2 | #2 | Alt: <n> steps left! | Solid stepping! |
| 3 | #3 | Only <n> steps away! | Crushed it! |
| 4 | random | 10 min to get <n> | Woo! 250/250 |
| 5 | random | Take me for a walk? | You won the hour! |
| 6 | random | Go for <n> more! | Easy peasy! |
| 7 | random | Feed me <n> steps! | Stepped and scored! |
| 8 | random | Up for <n> Steps? | Nailed it! |

TABLE 1-continued

| # | Order of Messages | Inactivity Messages | Congratulatory messages |
|---|---|---|---|
| 9 | random | <n> to win the hour! | Score - 250 more! |
| 10 | random | Wanna stroll? | 250 bites the dust |
| 11 | random | It's step o'clock! | Rocked that 250 |
| 12 | random | :D Let's roll | Hot stepper! |

Where <n> represents the number of steps left to meet the goal. Other embodiments may include other messages, such as the number of steps taken during the current hour. Further, in some embodiments, the messages may be location or situation aware, such as, "it stopped raining, let's go!" "You're almost at home, keep walking," "it's 7:55 PM, if you meet your hourly goal you will get the daily goal," etc.

In one embodiment, the messages may be downloaded from a server to the tracker (e.g., via a mobile device). This way, the messages keep changing to keep the experience fresh. For example, the server sends the message to the mobile device, and then the mobile device syncs with the tracker by transferring the new messages to the tracker.

Figure 5B:
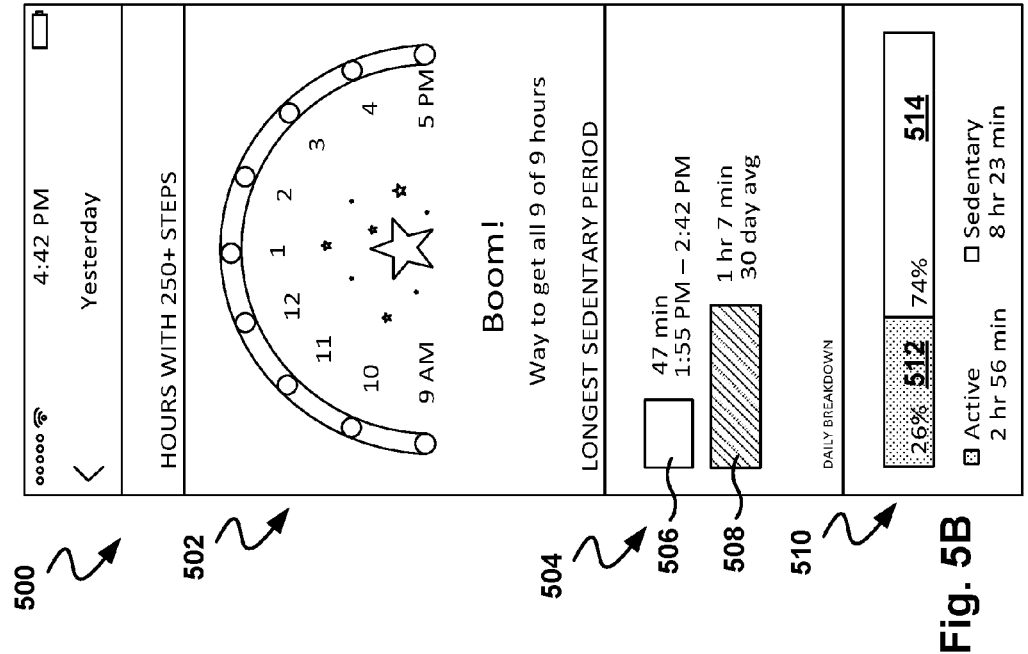
FIGS. 5A-5B illustrate the graphical user interface on the mobile device for presenting hourly goals and longest sedentary period, according to one embodiment.
Figure 5A:
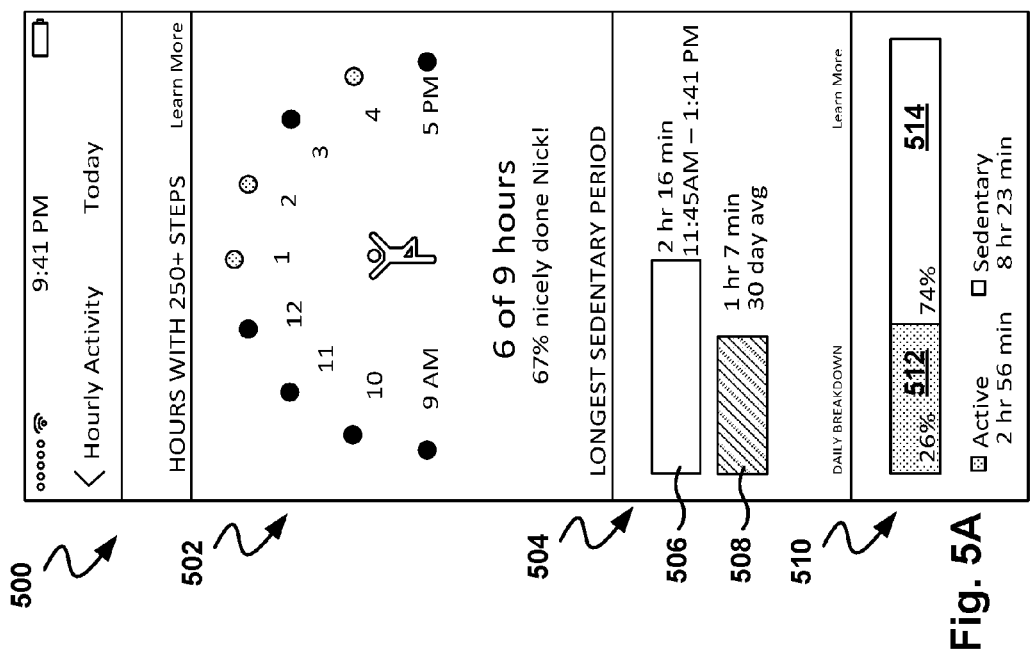

FIGS. 5A-5B illustrate the graphical user interface on the mobile device for presenting hourly goals and longest sedentary period, according to one embodiment. FIG. 5A illustrates interface 500 on a mobile device after the last interval of the day for hourly goals has expired.

The interface 500 includes an hourly-goal area 502, a longest-sedentary-period area 504, and a daily-breakdown area 510. In the hourly-goal area 502, the interface shows whether the goal for each hourly goal has been met or not met. When the goal has been met, the circle is filled with a first color (e.g., red) and if the goal has not been met, the circle is filled with a different color (e.g., grey). In one embodiment, the circles are laid out on an arc, and the icon used for hourly goals is in the center. Additionally, a message indicating how many hourly goals have been met (e.g., "6 of 9 hours") is presented, and a second message below providing additional information (e.g., "67% nicely done Nick!").

It is noted that the time of the day for hourly goals is configurable by the user, which is able to define a time box for hourly goals. In the exemplary embodiment of FIG. 5A, the user has selected a time box between 9 AM and 5 PM, but other time periods are possible. The number of circles corresponding to hours within the time box are then disposed equally spaced on the arc.

In some embodiments, a first goal of the GUIs described herein is to communicate an otherwise negative statistic in a positive way, and a second goal is to make the data as actionable as possible for the user. The graphic display for the hourly goals makes it easy to see if the user had "good" hours with step activity, and see when there were gaps which represented sedentary hours.

The sedentary time information accompanies inactivity alerts and gives users a sense for how active or sedentary users are during the day. For each day, the longest sedentary time is shown next to the last-30-day average for comparison. Area 504 for longest sedentary period includes two graph bars. The first bar 506 describes the longest sedentary period of the day, and a value is provided to the right of the bar indicating the actual length of the longest sedentary period (e.g., "2 hr 16 min") and the actual time of the longest sedentary period (e.g., "11:45 AM-1:41 PM").

The second bar 508 provides the 30-day average for the longest sedentary period, and the corresponding values to the right, the average duration (e.g., "1 hr 7 min") and a message indicating it is the 30 day average. The first bar and the second bar are drawn to the same scale in order to visually compare the longest sedentary period of the day to the 30-day average. It is noted that the measurement of the longest sedentary period does not include times when the user is sleeping or not wearing the activity tracking device.

Showing the longest sedentary period helps the user identify the time of the day where the user is less active. This way, the user can prioritize efforts to become more active during the time when the user is more sedentary.

Daily-breakdown area 510 includes a bar divided into two segments: a first segment 512 for the active time and a second segment 514 for the sedentary time (e.g., the total sedentary time S described in more detail below). The length of each of the segments is proportional to the actual percentage of time during the day when the user was active or sedentary, respectively. In the exemplary embodiment of FIG. 5A, the user was active 26% of the time and sedentary 74% of the time, therefore, the segment for stationary time is about three times the length of the segment for active time.

Below, a legend is presented indicating the color of the segments and if they are for active or sedentary times, and the actual amount of time when the user was active and sedentary (e.g., 8 hr 23 min).

As used herein, active time is the amount of time that the user is active during the day. In one embodiment, the total sedentary time S is calculated with the following equation:

$$S = 24 \text{ hrs} - \text{time not wearing tracker} - \text{time sleep} - \text{active time}$$

In some embodiments, the active time described herein may be calculated based on a comparison of measured MET values to a MET threshold, as described in more detail elsewhere in this disclosure.

In some embodiments, the system may determine that the activity tracking device is not being worn using various techniques, such as determining based on a motion sensor of the activity tracking device that the activity tracking device is too still or exhibits too little motion or activity to be worn. Further, the system may determine that the user is asleep based on motion associated with sleep being detected by the motion sensor of the activity tracking device. In some embodiments, the activity tracking device may include a heart rate sensor (such as an optical heart rate sensor), which can be used to detect when the activity tracking device is not being worn or the user is asleep. For example, if the heart rate sensor does not detect a heart rate signal, the system may determine that the activity tracking device is not being worn. Further, if the heart rate sensor detects a heart rate signal associated with a sleep pattern, the system may determine that the user is asleep.

In some embodiments, the longest sedentary period may detected by first detecting discrete sedentary periods throughout the day (e.g., periods where measured MET values always or mostly remain below a predetermined threshold, such as 2). The system then excludes from these detected sedentary periods any sub-portions where the device is off-wrist or the user is sleeping. The system will then select the longest remaining sedentary period as the longest sedentary period.

In some embodiments, the longest sedentary period is more specifically calculated by first identifying periods of time in a day (e.g., minute long intervals) where the user is always or mostly below a METS threshold. In some cases, the sedentary periods are able to span short moments of higher activity (e.g., as measured by higher METs values), as described in U.S. Provisional Patent Application No.

62/137,750, filed Mar. 24, 2015, and entitled "Sedentary Period Detection Utilizing a Wearable Electronic Device", which is herein incorporated by reference. Thereafter, the system described herein excludes, from the aforementioned sedentary periods, minutes where the user is asleep, or minutes where the device is off wrist and/or too still to be worn. The remaining sedentary minutes are then accumulated into contiguous sedentary periods (e.g., if at 3:59 pm and 4.31 pm the user's activity is classified as not sedentary, but if the user's activity is classified as sedentary for each of the minutes from 4 pm-4.30 pm, then the minutes from 4 pm-4.30 pm will be accumulated and classified as a single continuous sedentary period from 4 pm-4.30 pm). Of the remaining sedentary periods longer than a threshold value (e.g., longer than 10 minutes), the system selects the longest one as the longest sedentary period.

In some embodiments, the total sedentary time S is calculated as the summation of the sedentary periods detected in the process described above for identifying the longest sedentary period. In some embodiments, sedentary periods (detected in the process described above for identifying the longest sedentary period) that are shorter than 10 minutes, are classified as active time. Thus, in some embodiments, active time is detected based not only on METS being below or above a threshold, but also based on the relevant period being shorter or longer than some threshold length (e.g., 10 minutes). More information on determining active time is described in U.S. Provisional Patent Application No. 62/137,750, filed Mar. 24, 2015, and entitled "Sedentary Period Detection Utilizing a Wearable Electronic Device", which is herein incorporated by reference.

FIG. 5B illustrates interface 500 on the mobile device after the user has reached the daily goal. The exemplary interface is presented with the time box defined for tracking hourly goals. In this case, the time box ends at 5 PM, and at 4:42 PM the user meets the hourly goal for the last hour of the day.

Since the user has met all the hourly goals, a congratulatory message is displayed (e.g., "Boom!" and "Way to get all 9 of 9 hours"). In this embodiment, the hourly circles change color (e.g., to green) and are connected by a half-circle to signify that the daily goal has been reached. In this embodiment, the icon on area 502 is changed to a star, but other embodiments may include other icons.

FIGS. 6A-6D illustrate different interfaces of the GUI presented on the mobile device, according to one embodiment. Interface 602 is similar to the interface presented on the mobile tracking device. Interface 602 includes several areas for different activities, such as number of steps, heart rate, etc. The information presented on interface 602 is synced with the information on the activity tracking device.

Hourly-goal section 604 of interface 602 presents hourly-goal related information, with similar messages to the ones presented on the tracking device. For example, the message may be "3 of 9 hours with 250+", but it could be other messages, such as "Are you ready to move?" 606, "Are you moving each hour?" 608, "3 of 14 hours with 250+" 610, "8 of 9 hours with 250+" 612, "9 of 9 hours with 250+" 614, "0 of 250 steps this hour" 616, "59 of 250 steps this hour" 618, etc.

Figure 6A:
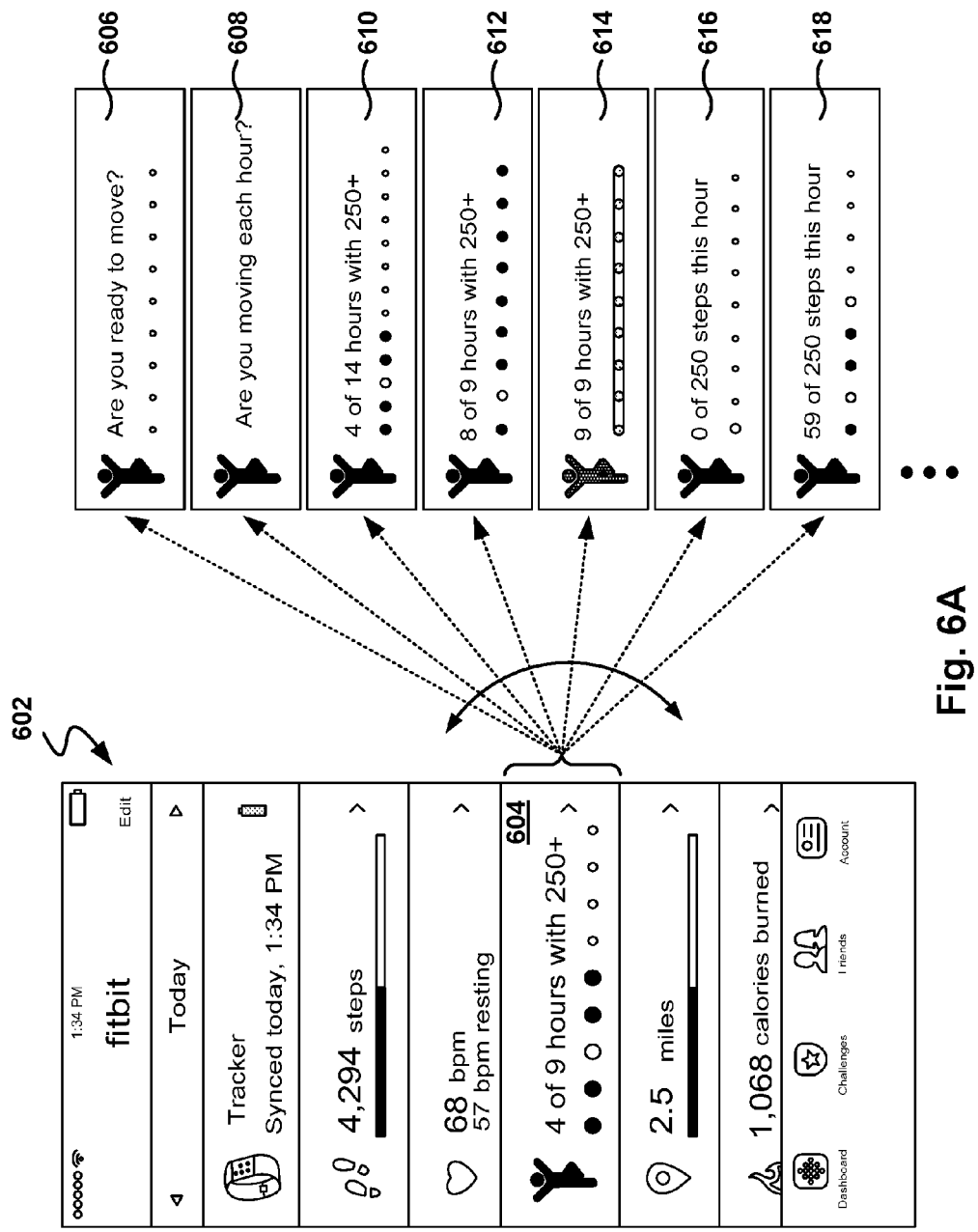
FIGS. 6A-6D illustrate different interfaces of the GUI presented on the mobile device, according to one embodiment.
Figure 6B:
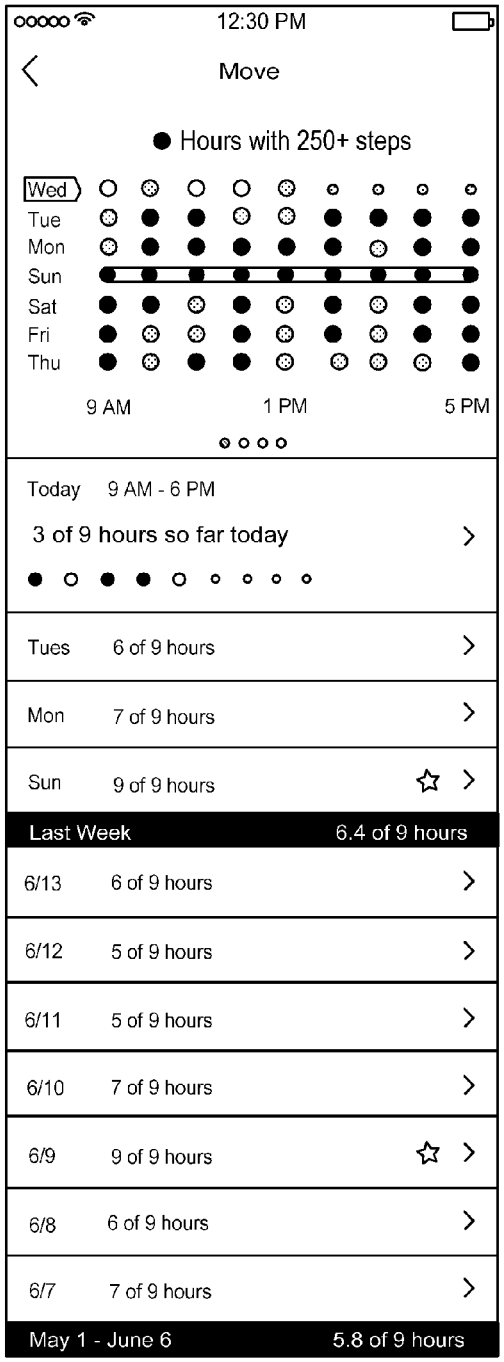

FIG. 6B is an interface presented on the mobile device that provides a summary of hourly-goal related achievements. The interface includes a graph representing the hours during the week when the hourly goal was reached, and below it, a list of days and the number of hours each day where the goal was reached.

The summary graph includes a matrix representation, or grid, of the hourly goals, where each hour is represented by a circle. If the goal was reached in that hour, the circle has a first color (e.g., red) and if the goal was not reached in that hour, the circle has a second color (e.g., black).

Each of the rows is for a different day and each column is for a different time of the day. The top row is for the current day (e.g., Wednesday in the exemplary embodiment) and the rows below show the previous days in descending order.

In one embodiment, if the daily goal is reached in one of the days, the matrix representation includes a line that joins the circles of that day representing that the daily goal was met (e.g., the daily goal was met on Sunday in FIG. 6B). In another embodiment, the circles of the current day have a different color than the circles from previous days for differentiation.

The grid representation quickly highlights patterns in hourly activity and when the user is not active. Further, the hourly presentation may be adjusted based on the time box defined by the user for tracking hourly goals.

In one embodiment, if the user selects one of the days listed below the grid representation, the details are provided for the hourly-goals reached during the selected day. Further, if the user scrolls down the list, the user gains access to older dates.

Figure 6C:
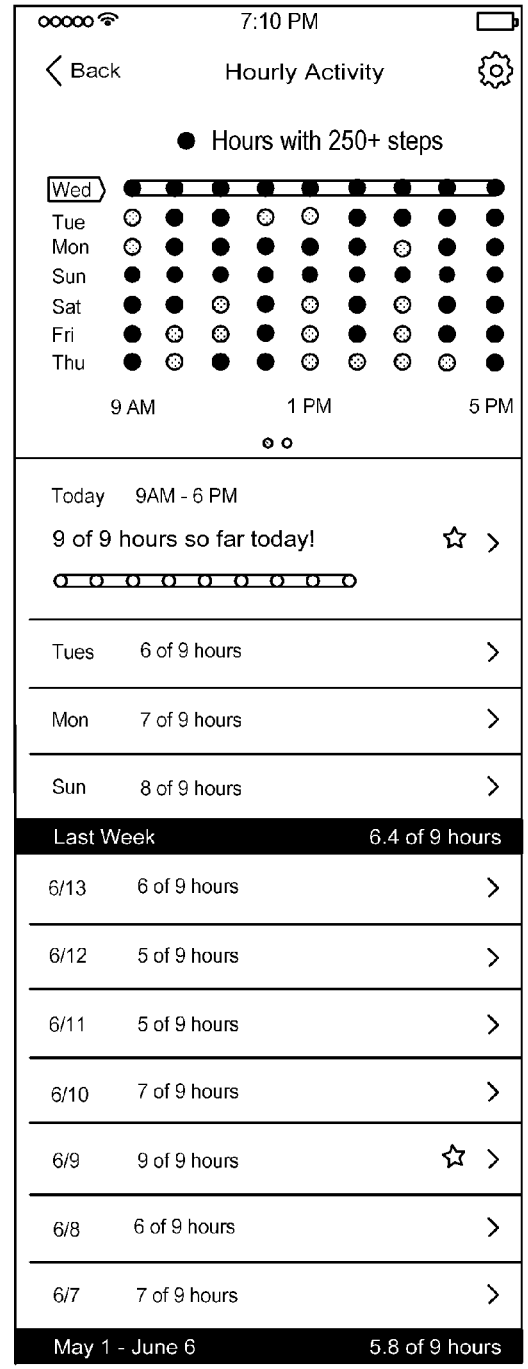

FIG. 6C illustrates a day when all the hourly goals have been reached. On the grid, the top row includes all the circles filled (e.g., in white) joined by a line to represent that the daily goal was met. Further, below the grid, the daily representation for the day shows the nine circles filled with the corresponding message, "9 of 9 hours today!" In one embodiment, a star is placed on the days where the daily goal is reached.

The interface of the mobile device allows the user to check hourly goals on the mobile device, such as how many steps the user needs to meet the goal for the current hour.

Figure 6D:
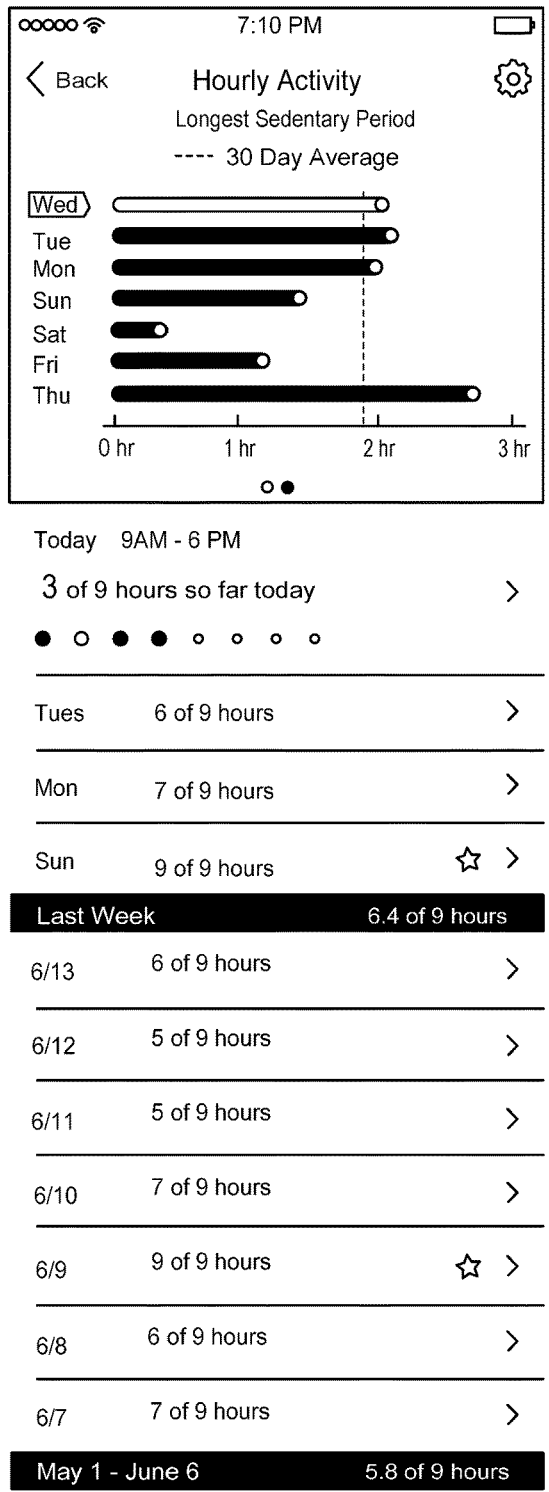

FIG. 6D shows an interface on the mobile device to present information regarding the longest sedentary period. On the top of the interface, a graph illustrates the longest sedentary day for each day of the week, together with the 30 day average of the longest sedentary day.

The graph is a bar graph with one horizontal bar for each day of the week. The length of the bars is proportional to the longest sedentary period for the day, and a vertical bar is added for the 30-day average.

FIGS. 7A-7E illustrate configuration screens of the GUI, according to one embodiment. Users can setup a schedule for defining when inactivity alerts are generated, including, days of the week, times per day, start and ending times, etc.

In one embodiment, the configuration of the activity tracking device is performed on a mobile device that synchronizes the data with the tracking device, and/or a central server that keeps a database of user information. In another embodiment, the user is able to configure the tracking device utilizing a web interface to access the server.

Figure 7A:
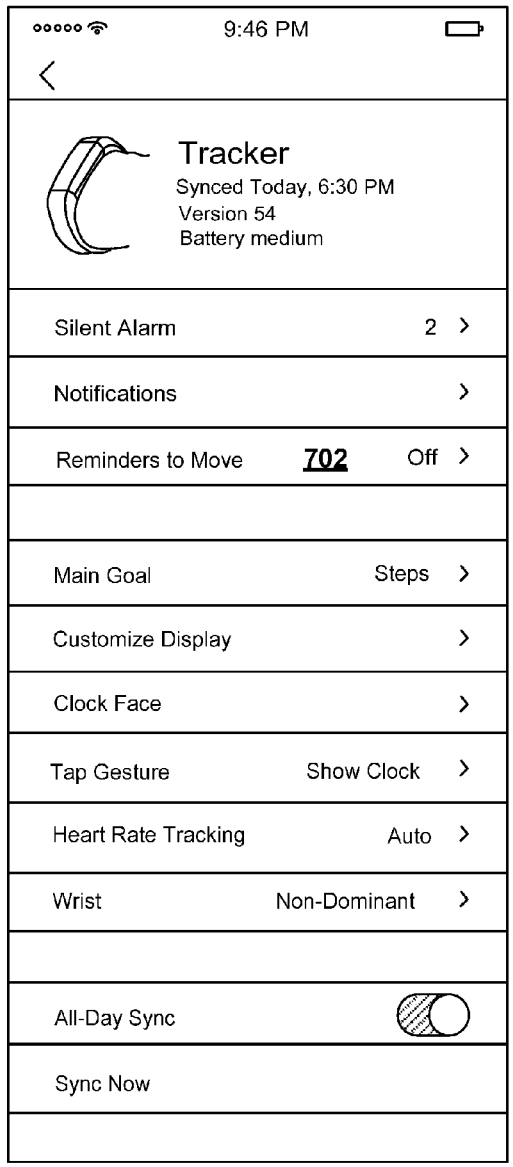

FIG. 7A is an interface presented on a mobile device for configuring fitness-related information and other profile information of the user. The configuration parameters may include configuring silent alarms, notifications, reminders to move 702 (e.g., hourly-goal-related parameters), goal for the day (e.g., number of steps to be taken during the day), the display, etc.

Figure 7B:
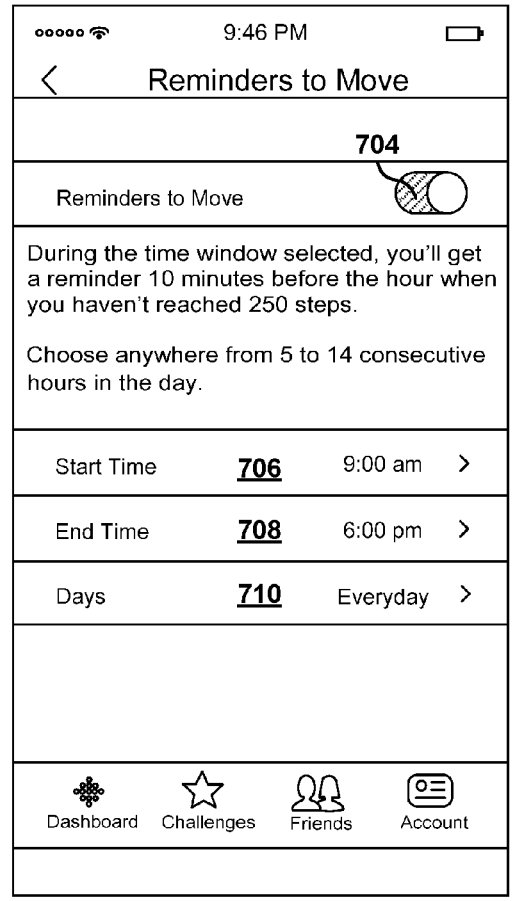

In the exemplary embodiment of FIG. 7A, a "Reminders to move" section 702 is presented for configuring parameters related to the hourly goals. If the user selects this option, the interface of FIG. 7B is presented.

The system allows the user to choose what hours in the day the user wants to track hourly goals to focus on being active, referred to herein as the time box. Therefore, the user does not have to meet hourly goals all the time, only the hours configured within the time box.

In one embodiment, the time box is customizable, meaning that the start time 706 and the end time 708 are customizable. However, in some embodiments, a minimum number of periods are required for tracking hourly goals (e.g., 5, 3, 7, but other values are also possible). Depending on the time box defined, the user interfaces will adapt to fit the time box. Further, the user is able to configure 710 in which days of the week the inactivity alerts will be provided.

Figures 7C, 7D, 7E:
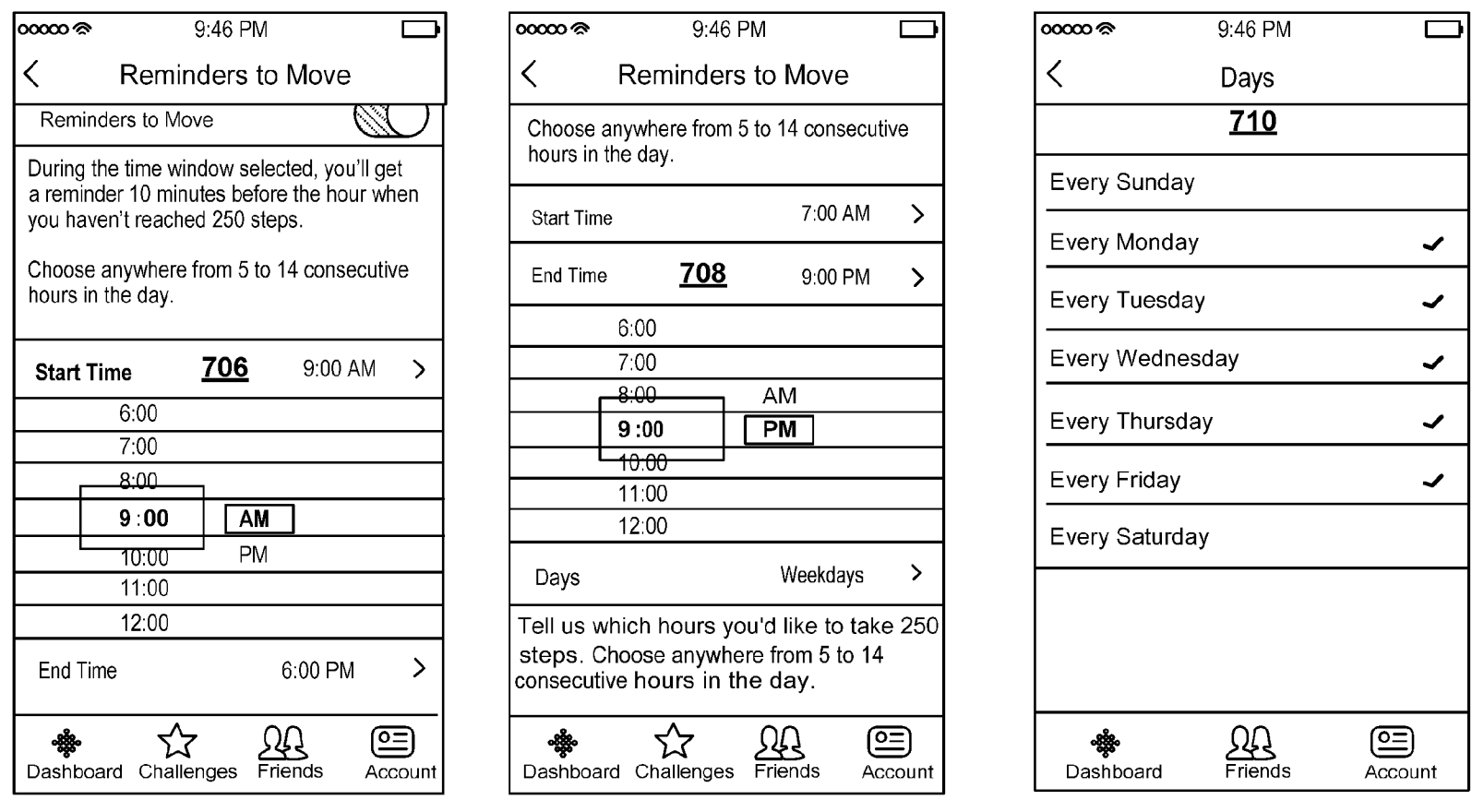

FIG. 7C illustrates the interface 706 for selecting the start time for the time box associated with the hourly goals, and FIG. 7D illustrates the interface 708 for configuring the end time of the time box. FIG. 7E illustrates the interface 710 for selecting which days of the week to enable hourly-goal tracking.

In other embodiments, it is also possible to define other intervals besides one hour for interval goal tracking. For example, the user may configure two-hour intervals, or 90-minute intervals, etc.

It is noted that the embodiments illustrated in FIGS. 5A-5B, 6A-6D, and 7A-7E are exemplary. Other embodiments may utilize different layouts, options, messages, etc. The embodiments illustrated should therefore not be interpreted to be exclusive or limiting, but rather exemplary or illustrative.

Figure 8C:
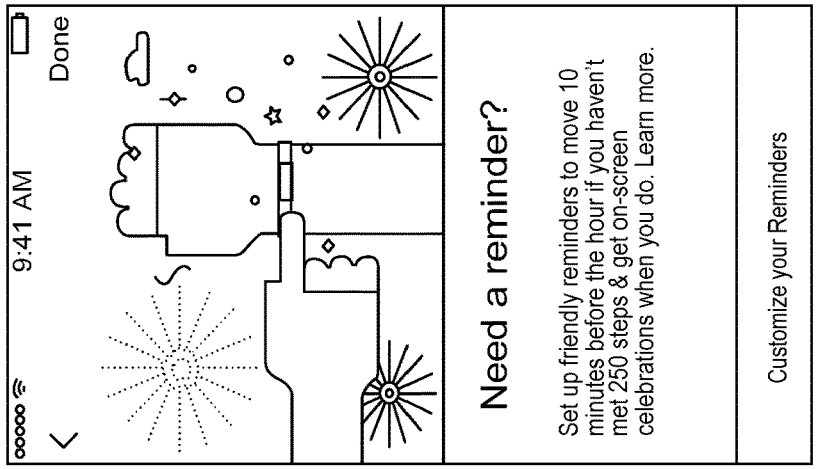
FIGS. 8A-8C are motivating messages for the user, according to one embodiment.
Figure 8B:
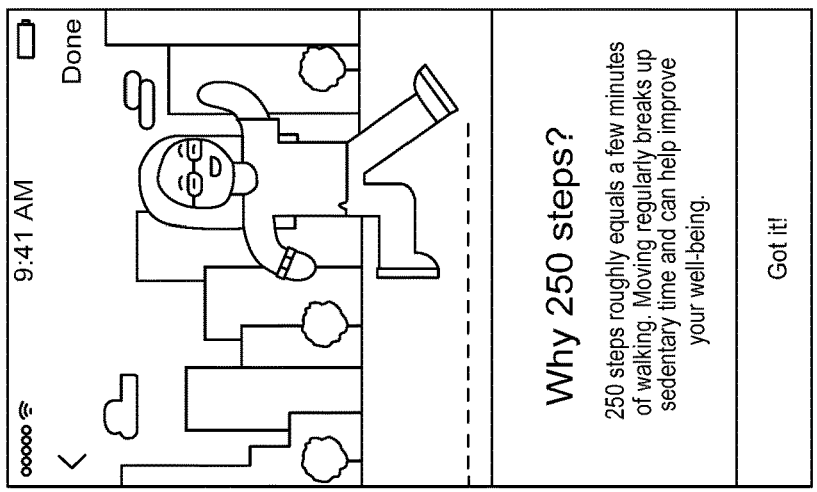
Figure 8A:
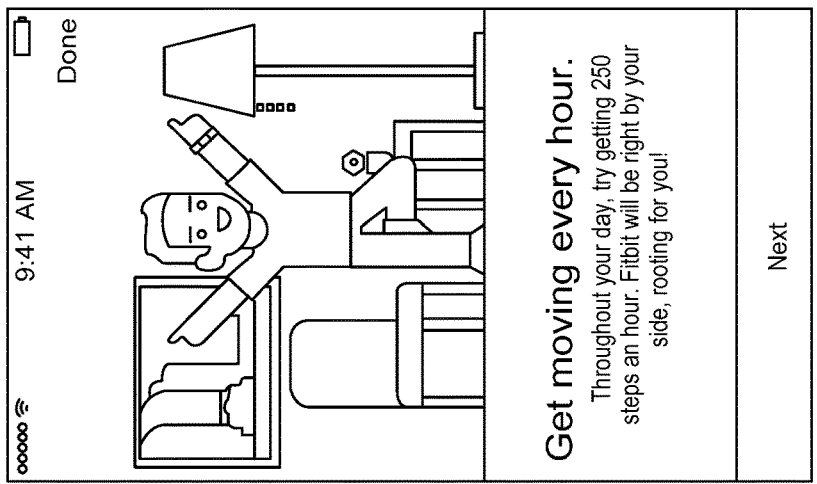

FIGS. 8A-8C are motivating messages for the user, according to one embodiment. FIG. 8A includes interface to encourage the user to walk every hour. Below a graphic with an active user, a motivated message states, "Get moving every hour."

Another message in a smaller font is presented below reciting, "Throughout your day, try getting 250 steps an hour. Fitbit will be right by your side, rooting for you!" This message is presented as an introduction to the user of the hourly-goal program to present inactivity alerts and longest sedentary time.

FIG. 8B illustrates an example of an interface to explain the user why it's important to keep active. A first message recites, "Why 250 steps?" A second message below in a smaller font recites, "250 steps roughly equals a few minutes of walking. Moving regularly breaks up sedentary time and can help improve your well-being." A button titled "Got it!" allows the user to move forward through the informational messages.

FIG. 8C is an interface introducing the concept of reminders for the hourly goals. A first message recites, "Need a reminder?" Another message below recites, "Set up friendly reminders to move 10 minutes before the hour if you haven't met 250 steps, and get on-screen celebrations when you do." A button titled, "Learn more," allows the user to obtain further information. A second button titled, "Customized your Reminders," opens the interface for configuring the reminders, as illustrated in FIGS. 7A-7E.

Figure 9A:
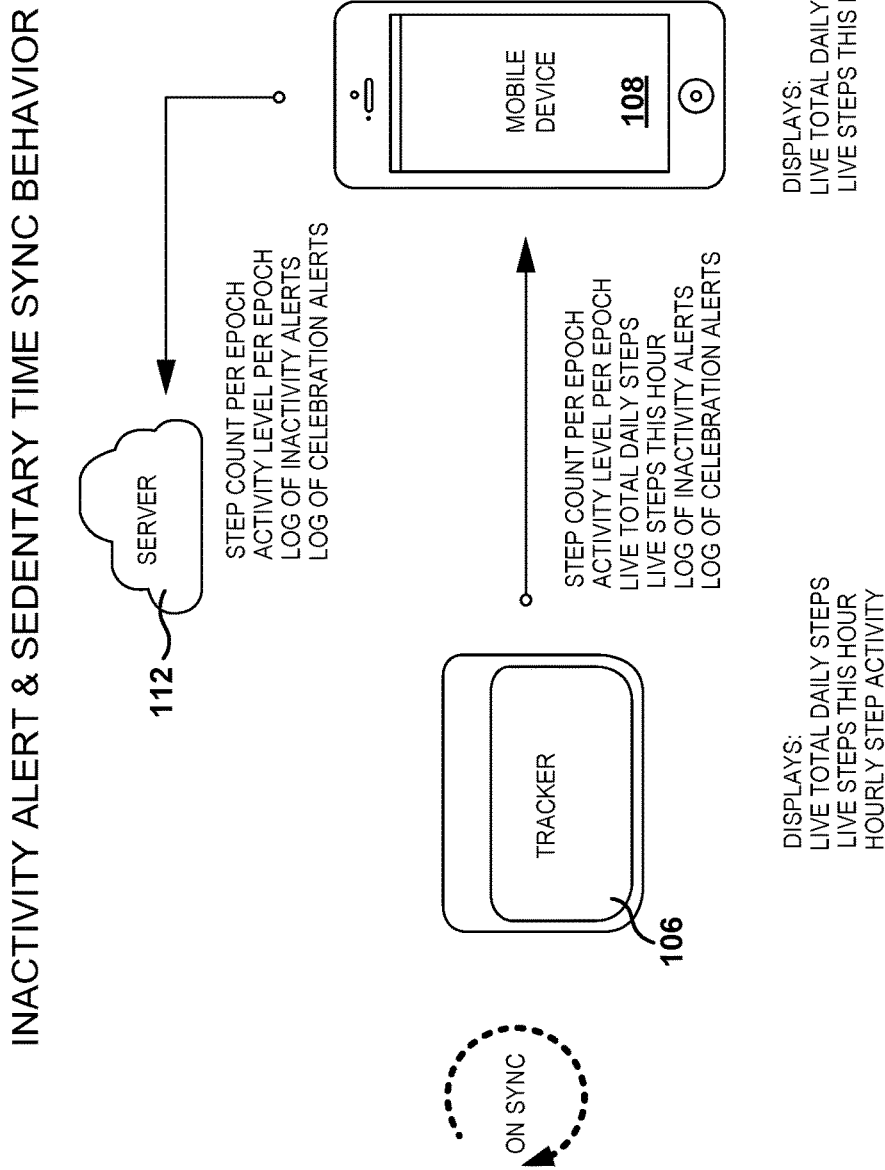
FIGS. 9A-9B illustrate the syncing of the activity tracking device with the mobile device, according to one embodiment.
Figure 9B:
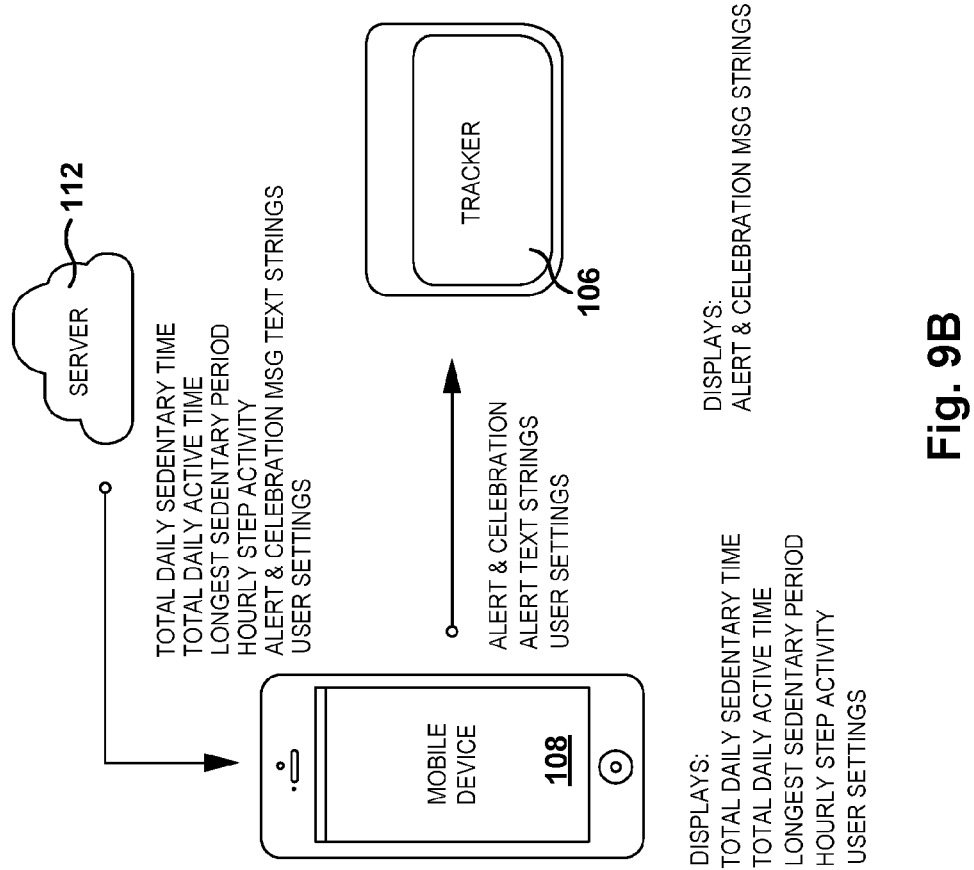

FIGS. 9A-9B illustrate the syncing of the activity tracking device with the mobile device, according to one embodiment. FIG. 9A illustrates the syncing of inactivity data, according to one embodiment. Tracker 106 synchronizes data with a mobile device 108, which then synchronizes the data from the tracker with server 112. In another embodiment (not shown) the tracker 106 may synchronize with the server via other devices, such as a personal computer, a laptop, etc.

During a sync, tracker 106 transmits data to mobile device 108, which is then synced to cloud-based server 112. The server then uses the most recent data to calculate key metrics (e.g., 30-day average sedentary period, longest sedentary period, etc.). The server transmits these key metrics and user settings back to the mobile device. In one embodiment, the server also transmits user settings and inactivity alert and celebration message text strings to the tracker via the mobile device.

For synchronization purposes, a period of time referred to as epoch is utilized, and the epoch corresponds to period of time associated with a configured frequency for synchronizing.

As illustrated in FIG. 9A, the tracker 106 may display information including the live total daily steps for the current day, the live steps this hour, and hourly step activity (e.g., describing whether the hourly goal was met for each hour in the day). When tracker 106 synchronizes with mobile device 108, the tracker sends one or more of the step count per epoch, activity level per epoch, the live total daily steps for the current day, the live steps this hour, a log of inactivity alerts (e.g., alerts already displayed by the tracker), and a log of celebration alerts (e.g., alerts already displayed by the tracker).

Mobile device 108 then syncs the data with server 112 and sends one or more of the step count per epoch, the activity level per epoch, the log of inactivity alerts, and the log of celebration alerts.

When the tracker and the mobile device are connected, the tracker transmits the live steps this hour and/or live total daily steps to the mobile device, enabling the mobile device to display this information. This allows the user to see each step taken this hour, or how many steps left to reach the hourly goal (e.g., "234 out of 250 steps this hour.")

FIG. 9B illustrates the syncing of sedentary-time information, according to one embodiment. In one embodiment, the server 112 calculates statistical parameters regarding the daily sedentary time and active time. In other embodiments (not shown), tracker 106 performs the statistical calculations, which allows the tracker to generate alerts even when there is no connection to the server or the mobile device.

When the tracker 106 synchronizes with server 112 via mobile device 108, the server 112 sends to the mobile device one or more of the total daily sedentary time, the total daily active time, the longest sedentary period, the hourly step activity, the alert and celebration message text strings, and user settings. As illustrated in FIG. 9B, the mobile device 108 may display the total daily sedentary time, the total daily active time, the longest sedentary period, the hourly step activity, and the user settings.

Afterwards, the mobile device sends the tracker one or more of the alert and congratulatory messages text strings, and the user settings. Tracker 106 then generates the inactivity alerts and congratulatory messages, as described above.

Figure 9C:
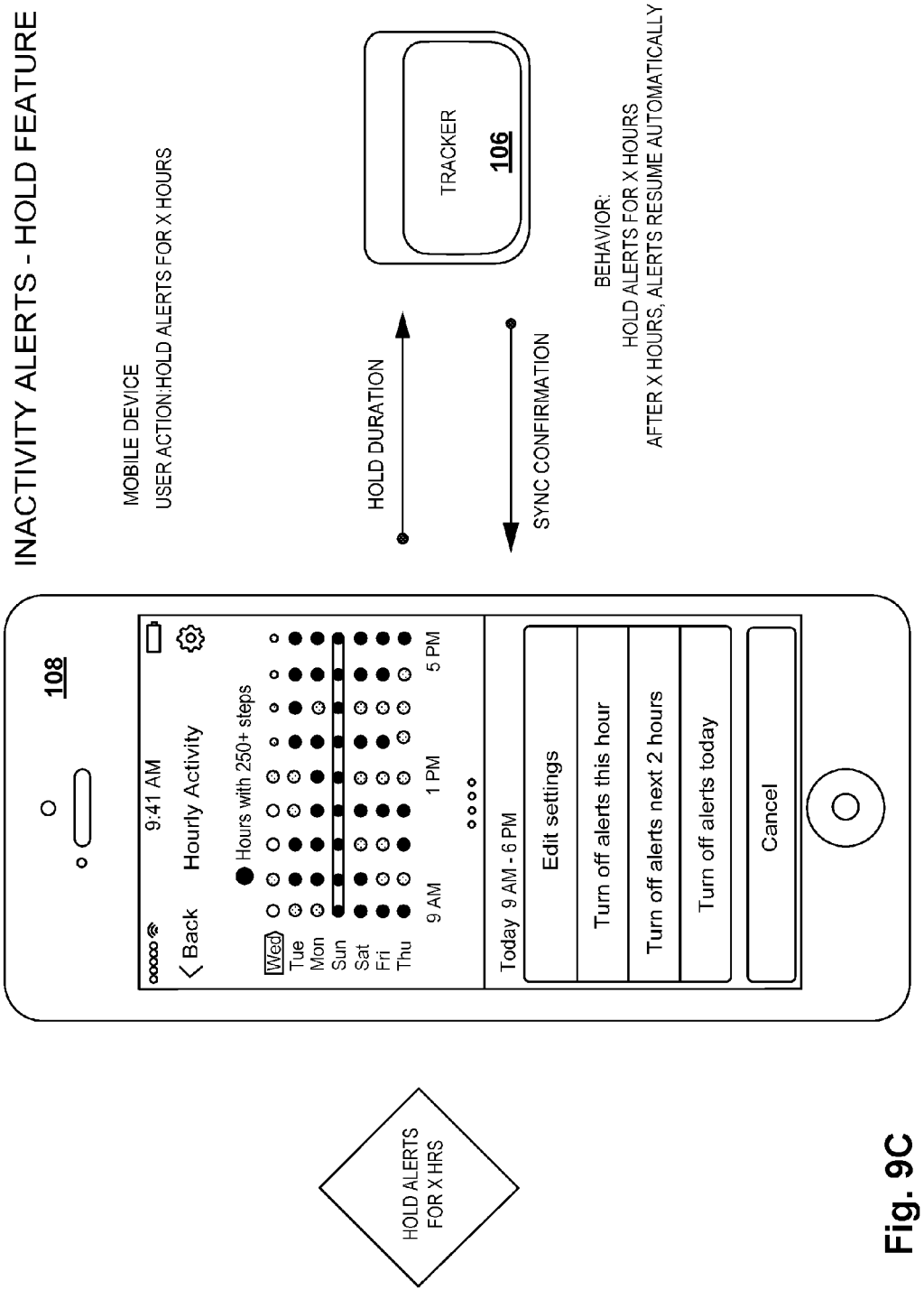
FIG. 9C illustrates a user interface for holding off inactivity alerts, according to one embodiment.

FIG. 9C illustrates a user interface for holding off inactivity alerts, according to one embodiment. In one embodiment, the user can configure the activity tracking device (e.g., via mobile device 108) to put alerts on hold, such as when the user is in a meeting. During the hold period, the tracker will not generate inactivity alerts or celebration messages.

After the hold period expires, the tracker will resume to automatically generate inactivity alerts without requiring user input to reconfigure the tracker, that is, the user does not need to remember to turn inactivity alerts back on. The tracker will continue to track inactivity data (e.g., steps taken this hour) through the hold period, but the tracker will not generate the inactivity alerts or celebration messages.

The ability to auto-resume inactivity alerts is important because users often forget to turn inactivity alerts back on again. Also, it is more convenient for the user to avoid having to reconfigure inactivity alerts.

In one embodiment, the mobile device interface includes an option for configuring the hold period. In one embodiment, the user is provided with four options: "Edit settings," "Turn off alerts this hour," "Turn off alerts next 2 hours," and "Turn off alerts today."

The "Edit settings" option allows the user to enter a different menu for configuring additional options, such as placing the device on hold for several days, or between specific times, a default amount of hold period, holidays, days of the week, etc.

If the user selects the option "Turn off alerts this hour," the inactivity alerts will be suspended for the remainder of present hour. For example, if it is 8:12 AM and the user turns off alerts for this hour, the alerts will be inactive until 9:00 AM.

If the user selects the option "Turn off alerts next two hours," the inactivity alerts will be suspended for the remainder of the present hour and the next hour. For example, if it is 8:12 AM and the user turns off alerts for two hours, the alerts will be inactive until 10:00 AM. If the user is currently in the last hour of the time box defined for inactivity alerts, selecting the option to turn off alerts for 2 hours will place a hold for the rest of the day, but not for the next tracked hour on the next day.

If the user selects the option "Turn off alerts today," the inactivity alerts will be suspended for the remainder of the day. For example, if it is 8:12 AM and the user turns off alerts for today, the alerts will be inactive until the beginning of the time box the next day.

In other embodiments, placing the hold on inactivity alerts may also be performed via user interface on the tracker device itself. For example, the user may select a "Settings" option, followed by an option to configure inactivity alerts, and then an option for "Hold." As in the case of the mobile device interface, the user may place a hold for this hour, the next 2 hours, today, etc.

It is noted that the embodiments illustrated in FIG. 9C are exemplary. Other embodiments may utilize different time periods, fewer or additional options (e.g., 3 hours), etc. The embodiments illustrated in FIG. 9C should therefore not be interpreted to be exclusive or limiting, but rather exemplary or illustrative.

In some embodiments, hold periods may also be generated when other conditions are met, such as when the user is having a meeting which is detected on a calendar application of the user. Also, if the user is asleep, no inactivity alerts are generated so the user is not disturbed. Further, no inactivity alerts are generated when the user is not wearing the tracker.

In another embodiment, the alerts are also placed on hold if it is determined that the user is already exercising, such as in a yoga class, or some other predefined activity. For example, the MET may indicate that the user is exercising but not taking steps. In this case, the inactivity alerts will be placed on hold. Additionally, inactivity alerts may be placed on hold for a predetermined amount of time after the user has finished exercising, because it may be annoying to receive reminders after the user has finished exercising (e.g., while the user is cooling-down or resting after exercising).

In addition, a hold period may be generated automatically by the tracker 106 when it is detected that the user has woken up within the current hour, which is being tracked for an hourly goal. If the user has had at least 15 minutes of sleep (other time periods are also possible) in the current hour, the inactivity alert will not be generated. For example, if the time box is defined between 7 AM and 5 PM, and the user gets up at 7:30 AM, then an alert is not generated at 7:50 AM because it would be a negative experience for the user (e.g., perhaps the user doesn't want to be bothered after getting up late on the weekend).

In another embodiment, the user is able to set "alert-free zones" based on location. For example, a configurable parameter may be set to stop the generation of inactivity alerts when the user is at a hospital, or at a church, or visiting a friend, etc.

In other embodiments, other hold periods may be defined. For example, the user may select to turn off alerts for exactly three hours. This way, if it is 12:55 PM and the user places a hold for exactly 3 hours, alerts will not be generated between 12:55 PM and 3:55 PM, and if at 3:55 PM the user has less than the hourly goal (e.g., 250 steps) then and inactivity alert will be generated at exactly 3:55 PM. In another embodiment, the user may select to turn of alerts for three hours, with the alerts resuming only at the start of the next full clock hour after the expiration of the three hours. For example, if it is 12:55 PM and the user places a hold for 3 hours, alerts will not be generated between 12:55 PM and 4 PM, and if at 4:55 PM the user has less than the hourly goal (e.g., 250 steps for the 4 PM-5 PM hourly interval), then an inactivity alert will be generated at exactly 4:55 PM.

Figure 10:
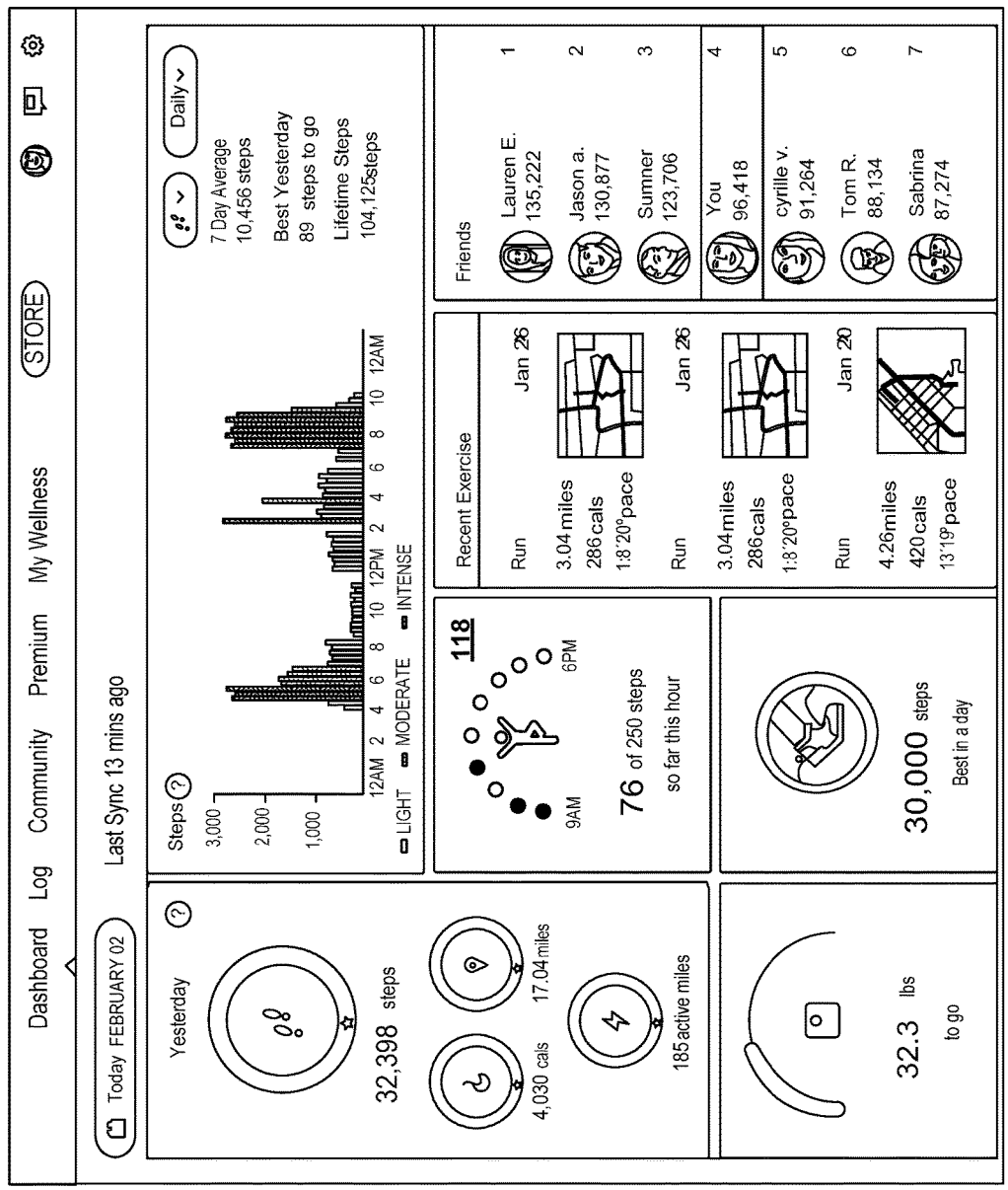
FIG. 10 is a dashboard of the user interface for presenting activity data, according to one embodiment.

FIG. 10 is a dashboard 116 of the user interface for presenting activity data, according to one embodiment. In one embodiment, dashboard 116 is accessed through a web interface, but other interfaces are also possible, such as a custom application executing on a PC, laptop, smart phone, tablet, etc.

The dashboard provides information related to the activity tracking device, and allows for configuration of the activity tracking device parameters. In addition, the dashboard provides statistical data, such as history over the last week, or month, graphs for daily heart rates, etc. Further yet, the dashboard provides a list of friends connected to the user, enabling for social activities associated with fitness.

The dashboard includes an area 118 that presents information regarding hourly goals and sedentary time, similar to the interfaces described above for a mobile device. For example, area 118 presents an icon for the hourly goals, with an arc above having circles corresponding to the hourly goals, and account of the steps taken in the current hour.

If the user selects area 118, a new page is open with more detailed information and configuration options (e.g., time box, hold periods, hourly goal, etc.). Further, the user is able to access social components for the inactivity tracking to challenge or compare achievements with friends.

In one embodiment, the user is able to send messages to friends, and these messages are presented if the hourly goal is not met, providing a more personal and fun experience. In addition, the system may present leaderboards, badges, cheering messages, taunting messages, etc. The viral interactions may also apply to sedentary time, for example, to challenge a friend on who has the shortest sedentary period for the day, or to challenge a friend on who has the shortest 30-day average for the longest sedentary period, etc.

Figure 11A:
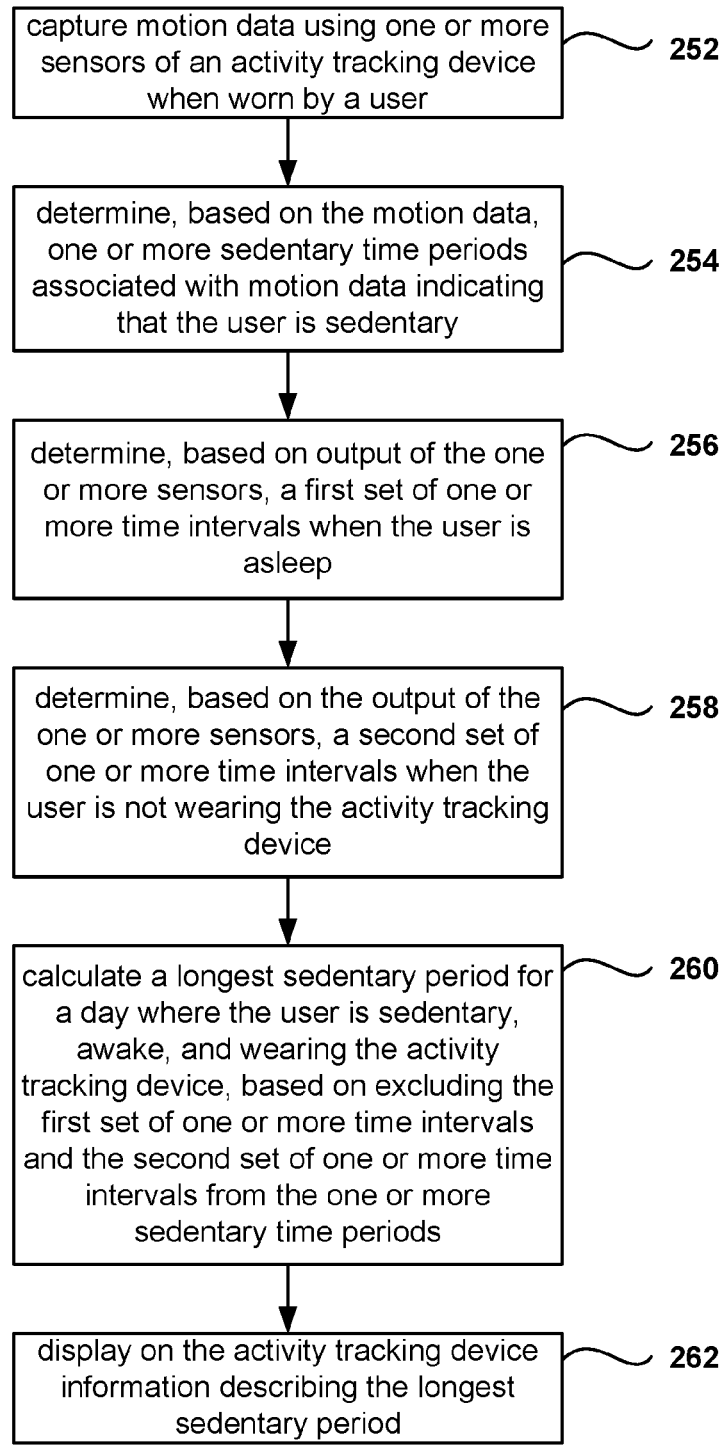
FIG. 11A is a flowchart of a method for reporting sedentary time information, according to one embodiment.

FIG. 11A is a flowchart of a method for reporting sedentary time information, according to one embodiment. While the various operations in this flowchart are presented and described sequentially, one of ordinary skill will appreciate that some or all of the operations may be executed in a different order, be combined or omitted, or be executed in parallel.

In operation 252, motion data is captured using one or more sensors of an activity tracking device when worn by a user. The sensors may be biometric sensors, or motion sensors, or any other type of sensor configured to detect user activity. From operation 252, the method flows to operation 254 for determining, based on the motion data, one or more sedentary time periods associated with motion data indicating that the user is sedentary.

From operation 254, the method flows to operation 256 for determining, based on output of the one or more sensors, a first set of one or more time intervals when the user is asleep. In operation 258, a second set of one or more time intervals when the user is not wearing the activity tracking device is determined, based on the output of the one or more sensors.

From operation 258, the method flows to operation 260 where the longest sedentary period for a day is calculated where the user is sedentary, awake, and wearing the activity tracking device, based on excluding the first set of one or more time intervals and the second set of one or more time intervals from the one or more sedentary time periods. From operation 260, the method flows to operation 262 for displaying on the activity tracking device information describing the longest sedentary period.

Figure 11B:
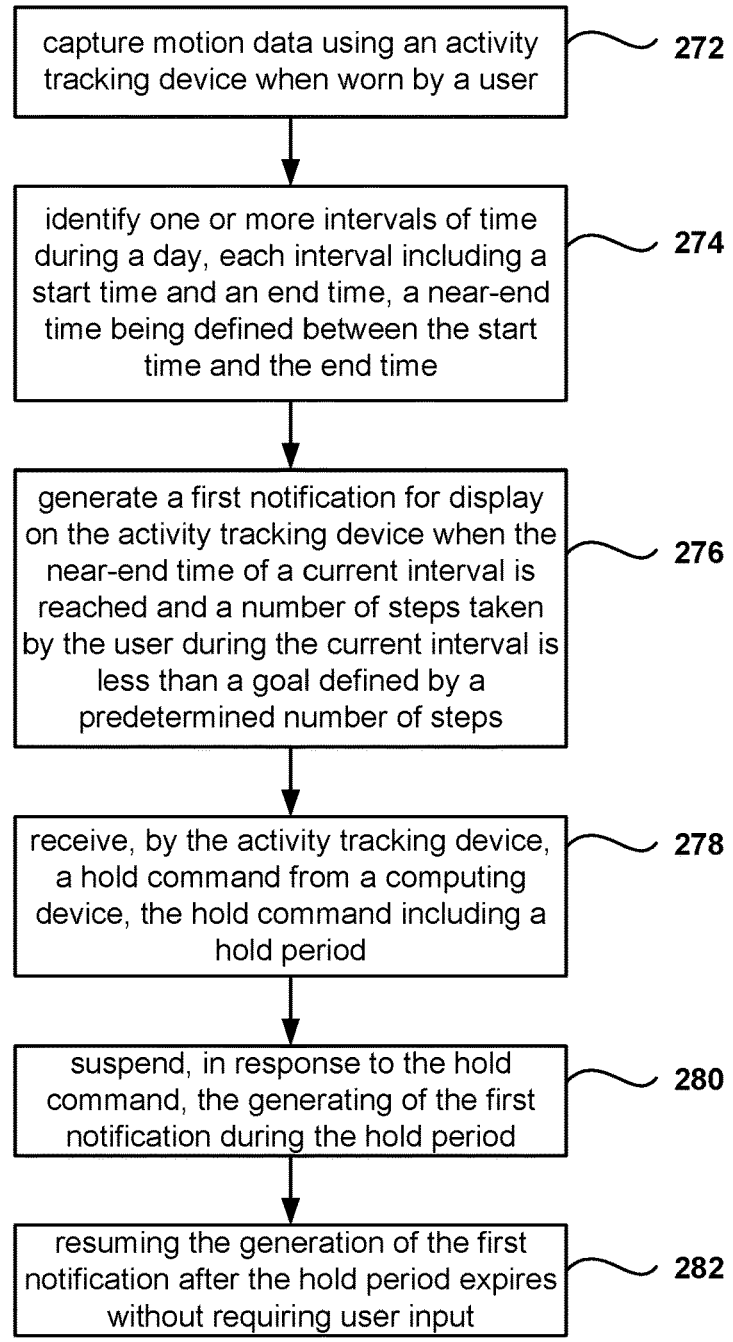
FIG. 11B is a flowchart of a method for holding the generation of alarm and congratulatory messages for a period of time, according to one embodiment.

FIG. 11B is a flowchart of a method for holding the generation of inactivity alerts and congratulatory messages for a period of time, according to one embodiment. While the various operations in this flowchart are presented and described sequentially, one of ordinary skill will appreciate that some or all of the operations may be executed in a different order, be combined or omitted, or be executed in parallel.

Operation 272 is for capturing motion data using an activity tracking device when worn by a user. From operation 272, the method flows to operation 274 where one or more intervals of time during a day are identified. Each interval includes a start time and an end time, where a near-end time is defined between the start time and the end time.

From operation 274, the method flows to operation 276 for generating a first notification for display on the activity tracking device when the near-end time of a current interval is reached and a number of steps taken by the user during the current interval is less than a goal defined by a predetermined number of steps.

Further, from operation 276, the method flows to operation 278 for receiving, by the activity tracking device, a hold command from a computing device, the hold command includes a hold period. In operation 280, the generating of the first notification is suspended during the hold period in response to the hold command.

From operation 280, the method flows to operation 282 where the generation of the first notification is resumed, without requiring user input, after the hold period expires.

Figure 11C:
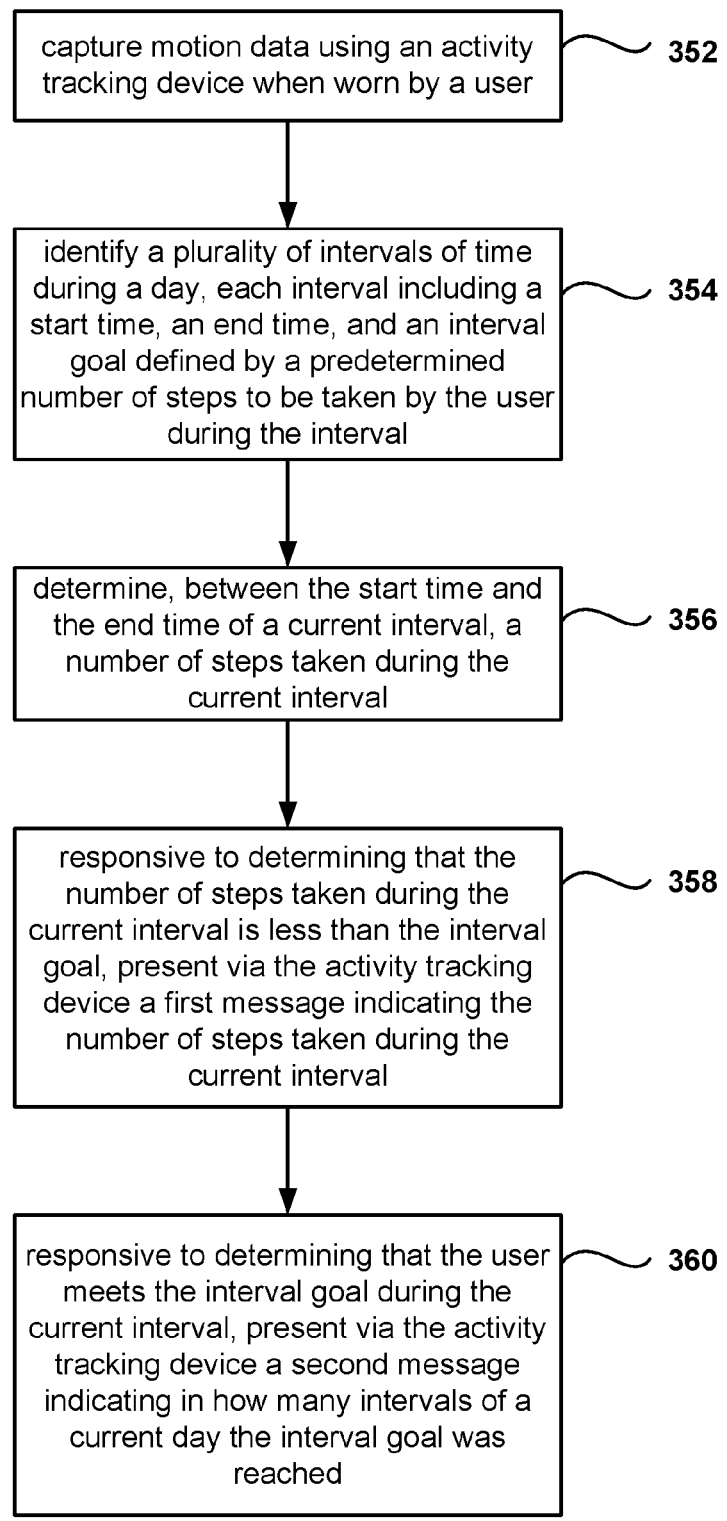
FIG. 11C is a flowchart of a method for reporting information regarding hourly steps, according to one embodiment.

FIG. 11C is a flowchart of a method for reporting information regarding hourly steps, according to one embodiment. While the various operations in this flowchart are presented and described sequentially, one of ordinary skill will appreciate that some or all of the operations may be executed in a different order, be combined or omitted, or be executed in parallel.

In operation 352, motion data is captured using an activity tracking device when worn by a user, and in operation 354, the method identifies a plurality of intervals of time during a day, each interval including a start time, an end time, and an interval goal defined by a predetermined number of steps to be taken by the user during the interval.

From operation 354, the method flows to operation 356 where the number of steps taken during the current interval is determined, between the start time and the end time of the current interval. From operation 356, the method flows to operations 358, and responsive to determining that the number of steps taken during the current interval is less than the interval goal, the activity tracking device presents a first message indicating the number of steps taken during the current interval. In an alternative embodiment, the first message indicates the number of steps left to meet the interval goal during the current interval.

From operation 358, the method flows to operation 360, where responsive to determining that the user meets the interval goal during the current interval, the activity tracking device presents a second message indicating in how many intervals of a current day the interval goal was reached.

Figure 11D:
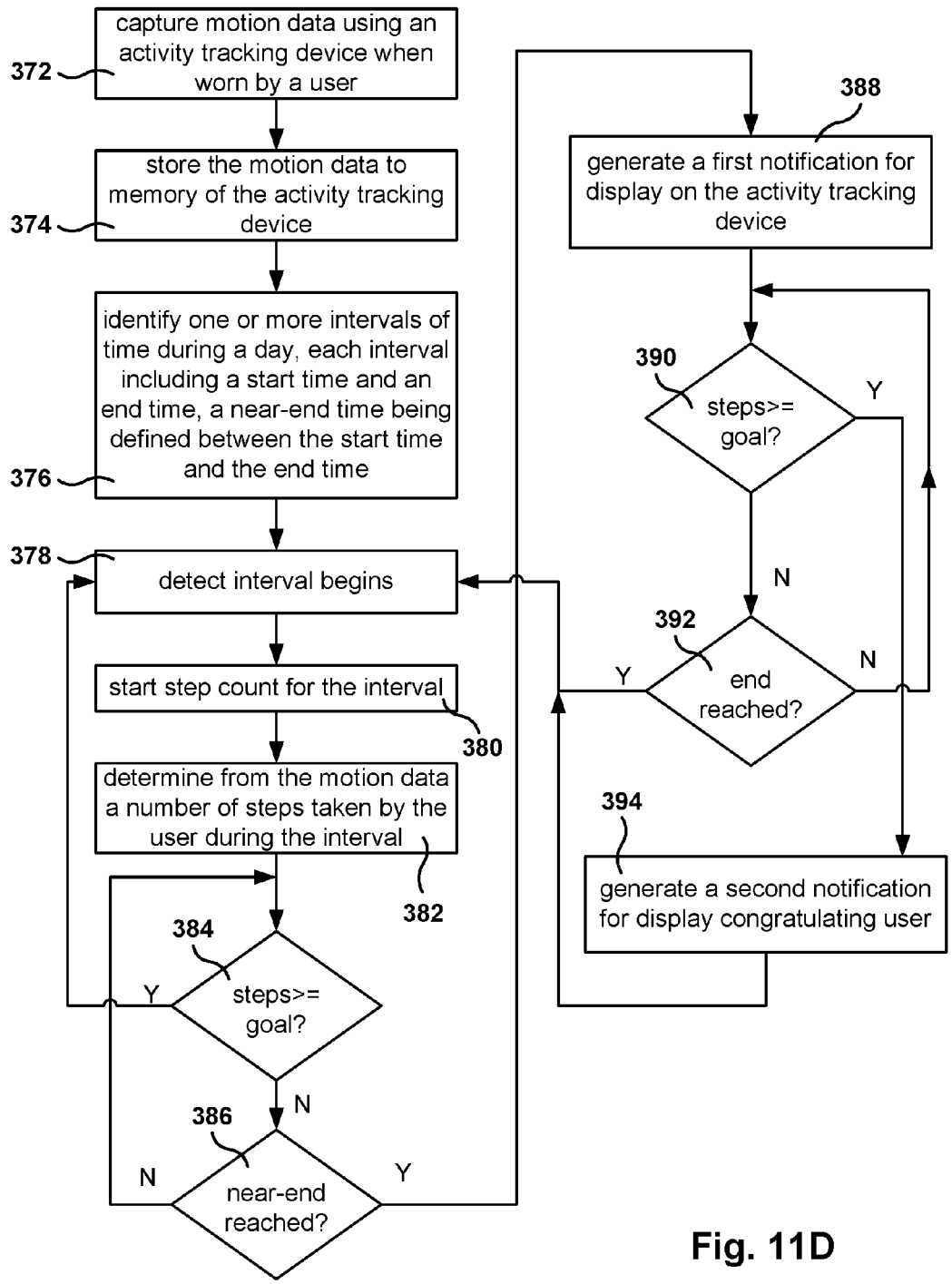
FIG. 11D is a flowchart of a method for generating alarms and congratulatory messages to reduce sedentary time, according to one embodiment.

FIG. 11D is a flowchart of a method for generating inactivity alerts and congratulatory messages to reduce sedentary time, according to one embodiment. While the various operations in this flowchart are presented and described sequentially, one of ordinary skill will appreciate that some or all of the operations may be executed in a different order, be combined or omitted, or be executed in parallel.

In operation 372, motion data is captured using an activity tracking device when the activity tracking device is worn by a user. From operation 372, the method flows to operation 374 where the motion data is stored in memory of the activity tracking device.

From operation 374, the method flows to operation 376 for identifying one or more intervals of time during a day. Each interval includes a start time and an end time, and a near-end time is defined between the start time and the end time. From operation 376, the method flows to operation 378 where the tracking device detects that an interval has begun.

From operation 378, the method flows to operation 380 where the step count for the interval is started. In operation 382 a determination is made of the number of steps taken by the user during the current interval based on the motion data.

From operation 382, the method flows to operation 384 where a check is made to determine if the number of steps taken is greater than or equal to a goal defined by a predetermined number of steps to be taken by the user during the interval. If the number of steps is greater than or equal to the goal, the method flows back to operation 378 to wait for the beginning of the next interval. This means, that no inactivity messages are generated if the user has met the goal during the current interval.

If the number of the steps is less than the goal, the method flows to operation 386 where another check is made to determine if the near-end time of the current interval has been reached (e.g., 10 minutes before the hour). If the near-end time has not been reached, the method flows back to operation 384, if the near-end time has been reached the method flows to operation 388, where a first notification is presented on the display of the activity tracking device.

From operation 388, the method flows to operation 390 where a check is made to determine if the number of steps taken during the current interval is greater than or equal to the goal. If so, the method flows to operation 394, where a second notification is presented on the display of the activity tracking device to congratulate the user for accomplishing the goal during the current interval.

If the check of operation 390 is negative, the method flows to operation 392 where a check is made to determine if the end of the interval has been reached. If the end of the interval has not been reached, the method flows back to operation 390, and if the end of the interval has been reached, the method flows back to operation 378 to wait for the beginning of the next interval. From operation 394, the method also flows back to operation 378 to wait for the beginning of the next interval.

Figure 12:
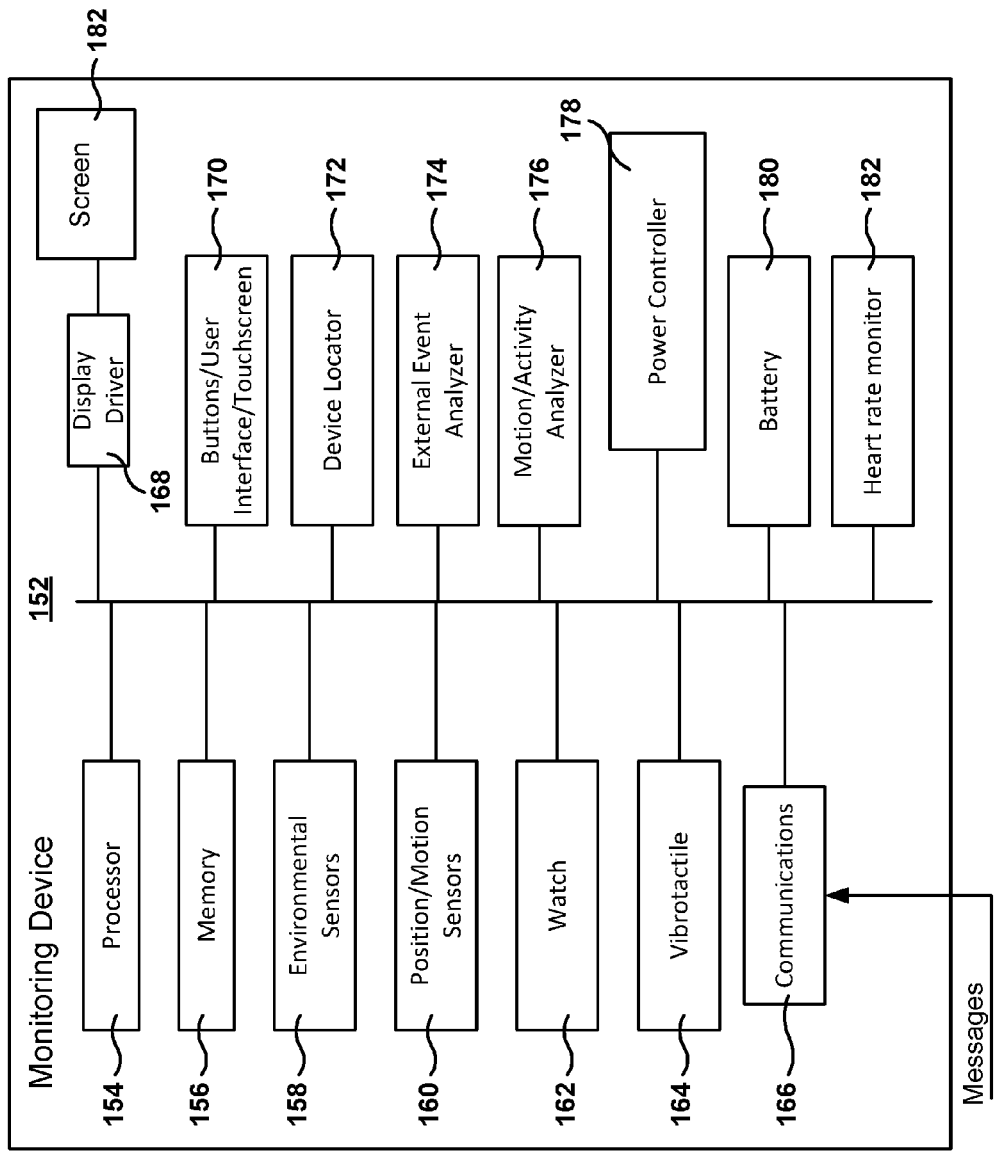
FIG. 12 is a simplified schematic diagram of a device for implementing embodiments described herein.

FIG. 12 is a simplified schematic diagram of a device for implementing embodiments described herein. The monitoring device 152 is an example of any of the monitoring devices described herein, and including a step tracker, a fitness tracker without buttons, or a fitness tracker defined to be clipped onto the belt of a user, etc. The monitoring device 152 includes processor 154, memory 156, one or more environmental sensors 158, one or more position and motion sensors 160, watch 162, vibrotactile feedback module 164, display driver 168, touchscreen 206, user interface/buttons 170, device locator 172, external event analyzer 174, motion/activity analyzer 176, power controller 178, battery 180, and heart rate monitor 182, all of which may be coupled to all or some of the other elements within monitoring device 152.

Examples of environmental sensors 158 include a barometric pressure sensor, a weather condition sensor, a light exposure sensor, a noise exposure sensor, a radiation exposure sensor, and a magnetic field sensor. Examples of a weather condition sensor include sensors for measuring temperature, humidity, pollen count, air quality, rain conditions, snow conditions, wind speed, or any combination thereof, etc. Examples of light exposure sensors include sensors for ambient light exposure, ultraviolet (UV) light exposure, or a combination thereof, etc. Examples of air quality sensors include sensors for measuring particulate counts for particles of different sizes, level of carbon dioxide in the air, level of carbon monoxide in the air, level of methane in the air, level of other volatile organic compounds in the air, or any combination thereof.

Examples of the position/motion sensor 160 include an accelerometer, a gyroscope, a rotary encoder, a calorie measurement sensor, a heat measurement sensor, a moisture measurement sensor, a displacement sensor, an ultrasonic sensor, a pedometer, an altimeter, a linear position sensor, an angular position sensor, a multi-axis position sensor, or any combination thereof, etc. In some embodiments, the position/motion sensor 160 measures a displacement (e.g., angular displacement, linear displacement, or a combination thereof, etc.) of the monitoring device 152 over a period of time with reference to a three-dimensional coordinate system to determine an amount of activity performed by the user during a period of time. In some embodiments, a position sensor includes a biological sensor, which is further described below.

The vibrotactile module 164 provides sensory output to the user by vibrating portable device 152. Further, the communications module 166 is operable to establish wired or wireless connections with other electronic devices to exchange data (e.g., activity data, geo-location data, location data, a combination thereof, etc.). Examples of wireless communication devices include, but are not limited to, a Wi-Fi adapter, a Bluetooth device, an Ethernet adapter, an infrared adapter, an ultrasonic adapter, etc.

The touchscreen 206 may be any type of display with touch sensitive functions. In another embodiment, a display is included but the display does not have touch-sensing capabilities. The touchscreen may be able to detect a single touch, multiple simultaneous touches, gestures defined on the display, etc. The display driver 168 interfaces with the touchscreen 206 for performing input/output operations. In one embodiment, display driver 168 includes a buffer memory for storing the image displayed on touchscreen 206. The buttons/user interface may include buttons, switches, cameras, USB ports, keyboards, or any other device that can provide input or output functions.

Device locator 172 provides capabilities for acquiring data related to the location (absolute or relative) of monitoring device 152. Examples device locators 172 include a GPS transceiver, a mobile transceiver, a dead-reckoning module, a camera, etc. As used herein, a device locator may be referred to as a device or circuit or logic that can generate geo-location data. The geo-location data provides the absolute coordinates for the location of the monitoring device 152. The coordinates may be used to place the monitoring device 152 on a map, in a room, in a building, etc. In some embodiments, a GPS device provides the geo-location data. In other embodiments, the geo-location data can be obtained or calculated from data acquired from other devices (e.g., cell towers, Wi-Fi device signals, other radio signals, etc.), which can provide data points usable to locate or triangulate a location.

External event analyzer 174 receives data regarding the environment of the user and determines external events that might affect the power consumption of the user. For example, the external event analyzer 174 may determine low light conditions in a room, and assume that there is a high probability that the user is sleeping. In addition, the external event analyzer 174 may also receive external data, such as GPS location from a smart phone, and determine that the user is on a vehicle and in motion.

In some embodiments, the processor 154 receives one or more geo-locations measured by the device locator 172 over a period of time and determines a location of the monitoring device 152 based on the geo-locations and/or based on one or more selections made by the user, or based on information available within a geo-location-location database of the network. For example, the processor 154 may compare the current location of the monitoring device against known locations in a location database, to identify presence in well-known points of interest to the user or to the community. In one embodiment, upon receiving the geo-locations from the device locator 172, the processor 154 determines the location based on the correspondence between the geo-locations and the location in the geo-location-location database.

The one or more environmental sensors 158 may sense and determine one or more environmental parameters (e.g., barometric pressure, weather condition, amount of light exposure, noise levels, radiation levels, magnetic field levels, or a combination thereof, etc.) of an environment in which the monitoring device is placed.

The watch 162 is operable to determine the amount of time elapsed between two or more events. In one embodiment, the events are associated with one or more positions sensed by the position sensor 160, associated with one or more environmental parameters determined by the environmental sensor 158, associated with one or more geo-locations determined by the device locator 172, and/or associated with one or more locations determined by the processor 154.

Power controller 178 manages and adjusts one or more power operational parameters defined for the monitoring device 152. In one embodiment, the power operational parameters include options for managing the touchscreen 206, such as by determining when to turn ON or OFF the touchscreen, scan rate, brightness, etc. In addition, the power controller 178 is operable to determine other power operational parameters, besides the parameters associated with the touchscreen, such as determining when to turn ON or OFF other modules (e.g., GPS, environmental sensors, etc.) or limiting the frequency of use for one or more of the modules within monitoring device 152.

Monitoring device 152 may have a variety of internal states and/or events which may dynamically change the characteristics of the touchscreen or of other modules. These states may include one or more of the following:

Battery level
Notifications/Prompting of user interaction
    Alarm
    Inactivity alert
    Congratulatory message
    Timer elapsed
    Email received/sent
    Instant Message received/sent
    Text message received/sent
    Calendar event
    Physiological goal met (e.g., 10,000 steps reached in the day)
    Non-physiological goal met (e.g., completed a to-do item)
    Application notifications
    Music player notifications (e.g., song ended/started, playlist ended/started)
User Interface
    Layout of virtual buttons on the touchscreen
    Expected user interaction based on what is displayed and/or the application in the foreground of the operating system.
        Expected user touch speed (e.g., fast for typing or playing a game, slow for reading an article)
        Expected user touch area
        Expected user touch trajectory (e.g., some games require long, straight swipes, while applications that take text input may require a touch to one specific area with little or no trajectory).
User interaction through non-touchscreen inputs
    User pressing a button
    User touching a capacitive touch sensor not integrated into the touchscreen
    User activating a proximity sensor
    Sensors which detect the user attempting to interact with the screen
        Force transducer under the screen
        Gyroscope, magnetometer, and/or accelerometer located near the screen
        Pressure transducer to measure change in pressure due to housing deflection when user presses on or near the screen
        Tap or initial touch detection using one or more or a combination of: accelerometers, piezoelectric sensors, motion sensors, pressure sensors, force sensors It is noted that these states may be communicated to the user through one or more methods including, but not limited to, displaying them visually, outputting an audio alert, and/or haptic feedback.

In some embodiments, data analysis of data produced by different modules may be performed in monitoring device 152, in other device in communication with monitoring device 152, or in combination of both devices. For example, the monitoring device may be generating a large amount of data related to the heart rate of the user. Before transmitting the data, the monitoring device 152 may process the large amount of data to synthesize information regarding the heart rate, and then the monitoring device 152 may send the data to a server that provides an interface to the user. For example, the monitoring device may provide summaries of the heart rate in periods of one minute, 30 seconds, five minutes, 50 minutes, or any other time period. By performing some calculations in the monitoring device 152, the processing time required to be performed on the server is decreased.

Some other data may be sent in its entirety to another device, such as steps the user is taken, or periodical updates on the location of the monitoring device 152. Other calculations may be performed in the server, such as analyzing data from different modules to determine stress levels, possible sickness by the user, etc.

It is noted that the embodiments illustrated in FIG. 12 are exemplary. Other embodiments may utilize different modules, additional modules, or a subset of modules. In addition, some of the functionality of two different modules might be combined in a single module, or the functionality of a single module might be spread over a plurality of components. The embodiments illustrated in FIG. 12 should therefore not be interpreted to be exclusive or limiting, but rather exemplary or illustrative.

More details regarding sedentary times and activity monitoring may be found in U.S. Provisional Patent Application No. 62/137,750, filed Mar. 24, 2015, and entitled "Sedentary Period Detection Utilizing a Wearable Electronic Device", and in U.S. patent application Ser. No. 14/156,413, filed Jan. 15, 2014, and entitled "Portable Monitoring Devices For Processing Applications and Processing Analysis of Physiological Conditions of a User associated with the Portable Monitoring Device." Both patent applications are herein incorporated by reference. The materials described in this patent applications may be combined with the embodiments presented herein.

Figure 13:
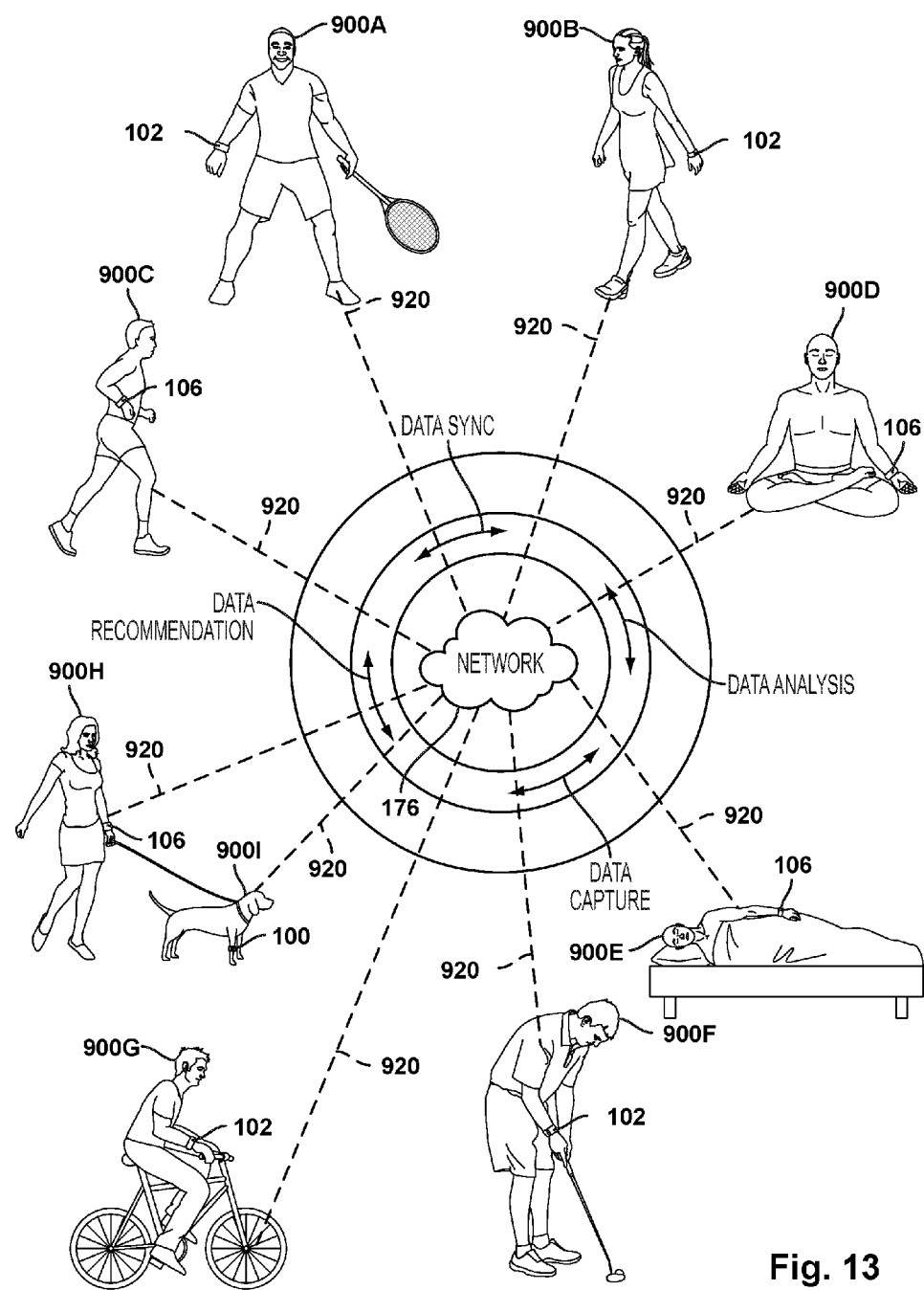
FIG. 13 illustrates an example where various types of activities of users can be captured or collected by activity tracking devices, in accordance with various embodiments.

FIG. 13 illustrates an example where various types of activities of users 900A-900I can be captured or collected by activity tracking devices, in accordance with various embodiments of the present embodiments. As shown, the various types of activities can generate different types of data that can be captured by the activity tracking device 102/106. The data, which can be represented as motion data (or processed motion data) can be transferred 920 to a network 176 for processing and saving by a server, as described above. In one embodiment, the activity tracking device 102/106 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 102/106 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (e.g., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 102/106 is received by the computing device, and the data is synchronized with the activity measured application on the server. In this example, data viewable on the computing device (e.g., smart phone) using an activity tracking application (app) can be synchronized with the data present on the server, and associated with the user's account.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In one embodiment, the sensor or sensors of a device 102/106 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 102/106 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor or biometric can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 102/106 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising:
    capturing motion data using a sensor of an activity tracking device including a processor, the activity tracking device configured to be worn by a user;
    storing by the processor the motion data to memory of the activity tracking device; identifying by the processor one or more intervals of time during a day, each interval including a start time and an end time, a near-end time being defined between the start time and the end time, the near-end time occurring at a predetermined period before the end time; and for each of the intervals:
    determining by the processor from the motion data a number of steps taken by the user during a corresponding interval;
    determining by the processor that the near-end time has been reached;
    determining by the processor that the number of steps taken by the user is within a threshold of a goal defined by a predetermined number of steps to be taken by the user during the corresponding interval;
    adjusting, by the processor, the near-end time based on the determination that the number of steps taken by the user is within the threshold; and
    in response to determining that the adjusted near-end time has been reached;
    determining by the processor that the number of steps taken by the user meets and/or exceeds the goal defined by the predetermined number of steps to be taken by the user during the corresponding interval; and
    generating by the processor a first notification for display on the activity tracking device when the near-end time has been reached,
    wherein the first notification is generated for each of the intervals.

2. The method of claim 1, wherein the first notification identifies a number of steps left to meet the goal during the corresponding interval.

3. The method of claim 1, further comprising:
    for each of the intervals, generating by the processor a second notification for display on the activity tracking device when the number of steps taken by the user during the corresponding interval reaches the goal before the end time.

4. The method of claim 3, wherein the second notification includes an accomplishment message indicating that the goal has been reached during the corresponding interval.

5. The method of claim 3, further comprising:
generating by the processor a first vibration by the activity tracking device when the first notification is generated; and
generating by the processor a second vibration by the activity tracking device when the second notification is generated.

6. The method of claim 1, further comprising:
connecting by the processor the activity tracking device to a computing device via a wireless connection; and
sending by the processor data stored in the memory of the activity tracking device to the computing device, the data including information regarding the number of steps taken during one or more of the intervals, the information being used by the computing device to present a graphical display that identifies each of the intervals and identifies specific ones of the intervals in which the goal was reached.

7. The method of claim 6, further comprising:
receiving by the processor, from the computing device, a time box setting that identifies the start time of an earliest interval of the one or more intervals and the end time of a latest interval of the one or more intervals.

8. The method of claim 1, further comprising:
processing by the processor data stored in the memory of the activity tracking device to identify information regarding the number of steps taken during each of the one or more intervals; and
displaying by the processor on a screen of the activity tracking device a graphical representation of each of the intervals, the graphical representation including a visual cue that identifies the intervals and if the goal was reached or not reached in each of the intervals.

9. The method of claim 1, wherein each interval is an hour, wherein the start time for each of the intervals is a time of the day when the corresponding hour begin.

10. The method of claim 9, wherein the near-end time is the start time plus at least three quarters of a duration of the corresponding interval.

11. The method of claim 1, further comprising:
processing by the processor data stored in the memory of the activity tracking device to identify information regarding the number of steps taken during each of the one or more intervals; and
displaying by the processor on a screen of the activity tracking device progress data that indicates in how many of completed intervals of a present day the goal has been reached.

12. The method of claim 1, further comprising:
processing by the processor data stored in the memory of the activity tracking device to identify information regarding the number of steps taken during each of the one or more intervals; and
displaying by the processor, after the end time of a last interval of the day, on a screen of the activity tracking device an end of day summary that indicates in how many of the intervals the goal was reached for the day.

13. The method of claim 1, further comprising:
processing by the processor data stored in the memory of the activity tracking device to identify information regarding the number of steps taken during each of the one or more intervals; and
displaying by the processor on a screen of the activity tracking device a complete message indicating for each of the intervals of the day if the goal was reached or not.

14. The method of claim 1, further comprising:
processing by the processor data stored in the memory of the activity tracking device to identify information regarding the number of steps taken during each of the one or more intervals; and
displaying by the processor on a screen of the activity tracking device a daily-goal message indicating that the goal has been reached in all the intervals of the day.

15. The method of claim 1, further comprising:
connecting by the processor the activity tracking device to a computing device via a wireless connection; and
sending by the processor data stored in the memory of the activity tracking device to the computing device, the data including information regarding the number of steps taken during one or more of the intervals, the information being used by the computing device to present a graphical display with a history that recites if the goal was reached in each of the intervals.

16. The method of claim 15, wherein the history is graphically presentable on the computing device for a selected day, the graphical display including a discrete visual indicator for each interval of the selected day.

17. The method of claim 16, wherein the history is graphically presentable for a number of days in a week, each day including the discrete visual indicators for the intervals in the respective day.

18. The method of claim 17, wherein the discrete visual indicators are arranged in a grid, wherein each row of the grid is associated with a respective day and each column of the grid is associated with a respective interval.

19. The method of claim 16, wherein the data received by the computing device from the activity tracking device is further used by the computing device to enable display of metrics that identify a count of number of intervals of a day where the goal was reached.

20. The method of claim 19, wherein the count of number of intervals of a day where the goal was reached is displayable for specific calendar dates.

21. The method of claim 1, wherein the first notification is an inactivity alert that is indicative of not yet reaching the goal.

22. The method of claim 21, wherein the inactivity alert includes one or more of a text message, an audible sound, and a vibration.

23. The method of claim 3, wherein the second notification is a celebration notification that is indicative of reaching the goal, wherein the celebration notification includes one or more of a text message, an audible sound, and a vibration.

24. The method of claim 1, further comprising:
connecting by the processor the activity tracking device to a computing device via a wireless connection, the computing device having a connection to a server that stores data for the activity tracking device;
receiving by the processor a plurality of text strings from the computing device; and
storing by the processor the plurality of text strings to the memory of the activity tracking device.

25. The method of claim 24, further comprising:
selecting by the processor one of the plurality of text strings for presentation in the first notification, the first notification being an inactivity alert.

26. The method of claim 25, wherein a first set of the text strings for the inactivity alert are set for display in a predefined order and a second set of the text strings for the inactivity alert are set for display in a randomly generated order.

27. The method of claim 24, further comprising:
selecting by the processor one of the plurality of text strings for presentation in a second notification, the second notification being a celebration notification that the goal has been reached.

28. A method, comprising:
capturing motion data using a sensor of an activity tracking device including a processor, the activity tracking device configured to be worn by a user;
storing by the processor the motion data to memory of the activity tracking device; identifying by the processor an interval of time having a start time and an end time, wherein a near-end time is defined between the start time and the end time, the near-end time occurring at a predetermined period before the end time;
determining by the processor from the motion data a number of steps taken by the user during the interval;
determining by the processor that the near-end time has been reached; determining by the processor that the number of steps taken by the user is within a threshold of a goal defined by a predetermined number of steps to be taken by the user during the corresponding interval;
adjusting, by the processor, the near-end time based on the determination that the number of steps taken by the user is within the threshold; and
in response to determining that the adjusted near-end time has been reached;
determining by the processor that the number of steps taken by the user meets and/or exceeds the goal defined by the predetermined number of steps to be taken by the user during the corresponding interval; and
generating by the processor a first notification for display on the activity tracking device when the near-end time has been reached,
wherein the first notification is generated for each of the intervals.

29. The method of claim 28, further comprising:
generating by the processor a second notification for display on the activity tracking device when the number of steps taken by the user during the interval reaches the goal before the end time,
wherein the first notification identifies a number of steps left to meet the goal during the interval,
wherein the second notification includes an accomplishment message indicating that the goal has been reached during the interval.

30. A non-transitory computer-readable storage medium having stored thereon instructions that, when executed, cause a processor of a computing device to:
capture motion data using a sensor of an activity tracking device including a processor, the activity tracking device configured to be worn by a user;
store the motion data to a memory of the activity tracking device;
identify one or more intervals of time during a day, each interval including a start time and an end time, a near-end time being defined between the start time and the end time, the near-end time occurring at a predetermined period before the end time;
and for each of the intervals:
determine from the motion data by the processor a number of steps taken by the user during a corresponding interval;
determine that the near-end time has been reached;
determine that the number of steps taken by the user is within a threshold of a goal defined by a predetermined number of steps to be taken by the user during the corresponding interval;
adjust the near-end time based on the determination that the number of steps taken by the user is within the threshold; and
in response to the adjusted near-end time being reached;
determine that the number of steps taken by the user meets and/or exceeds the goal defined by the predetermined number of steps to be taken by the user during the corresponding interval; and
generate a first notification for display on the activity tracking device when the near-end time has been reached,
wherein the first notification is generated for each of the intervals.

* * * * *

UNITED STATES PATENT AND TRADEMARK OFFICE
CERTIFICATE OF CORRECTION

PATENT NO. : 10,080,530 B2  
APPLICATION NO. : 15/048980  
DATED : September 25, 2018  
INVENTOR(S) : Yeqing Cheng et al.

Page 1 of 1

It is certified that error appears in the above-identified patent and that said Letters Patent is hereby corrected as shown below:

In the Claims

Column 29, Line 38 In Claim 9, the word 'begin' should be changed to --begins--.

Signed and Sealed this
Third Day of September, 2019

Andrei Iancu
*Director of the United States Patent and Trademark Office*